(12) United States Patent
Ursin et al.

(10) Patent No.: US 8,378,186 B2
(45) Date of Patent: Feb. 19, 2013

(54) EXPRESSION OF FATTY ACID DESATURASES IN CORN

(75) Inventors: Virginia Ursin, Pawcatuck, CT (US); Byron Froman, Davis, CA (US); A. J. Nava, Woodland, CA (US); Jennifer Gonzales, Woodland, CA (US)

(73) Assignee: Monsanto Technology LLC, St. Louis, MO (US)

( * ) Notice: Subject to any disclaimer, the term of this patent is extended or adjusted under 35 U.S.C. 154(b) by 502 days.

(21) Appl. No.: 11/578,447

(22) PCT Filed: Apr. 15, 2005

(86) PCT No.: PCT/US2005/012778
§ 371 (c)(1),
(2), (4) Date: Jun. 20, 2008

(87) PCT Pub. No.: WO2005/102310
PCT Pub. Date: Nov. 3, 2005

(65) Prior Publication Data
US 2008/0260929 A1  Oct. 23, 2008

Related U.S. Application Data

(60) Provisional application No. 60/563,135, filed on Apr. 16, 2004.

(51) Int. Cl.
*A01H 5/00* (2006.01)
*C12N 1/20* (2006.01)
*C12N 15/82* (2006.01)
*C07H 21/02* (2006.01)
*C07H 21/04* (2006.01)

(52) U.S. Cl. ............ 800/320.1; 800/295; 800/298; 800/281; 800/313; 800/306; 435/419; 435/252.3; 435/134; 530/300; 530/350; 536/23.1; 536/23.2; 426/601; 426/623; 426/630; 426/615

(58) Field of Classification Search .......... 426/601
See application file for complete search history.

(56) References Cited

U.S. PATENT DOCUMENTS

| 3,488,198 A | 1/1970 | Bundus |
| 3,676,157 A | 7/1972 | Wintersdorff et al. |
| 4,273,790 A | 6/1981 | Bosco et al. |

(Continued)

FOREIGN PATENT DOCUMENTS

| AU | 2003206846 | 2/2003 |
| EP | 0 537 178 | 8/1994 |

(Continued)

OTHER PUBLICATIONS

Conti et al., "γ-linolenic acid production by solid-state fermentation of mucorales strains on cereals," *Bioresource Technology*, 76:283-286, 2001.

(Continued)

*Primary Examiner* — Chhaya Sayala
*Assistant Examiner* — Assaf Zilbering
(74) *Attorney, Agent, or Firm* — SNR Denton US LLP; Byron V. Olsen Esq.

(57) ABSTRACT

The invention relates generally to the expression of desaturase enzymes in transgenic corn plants and compositions derived therefrom. In particular, the invention relates to the production of oils with improved omega-3 fatty acid profiles in corn plants and the seed oils produced thereby. Such oils may contain stearidonic acid, which is not naturally found in corn plants and has been shown to have beneficial effects on health.

7 Claims, 3 Drawing Sheets

U.S. PATENT DOCUMENTS

| | | | |
|---|---|---|---|
| 4,757,011 A | 7/1988 | Minekus et al. | |
| 4,776,984 A | 10/1988 | Traitler et al. | 260/412.2 |
| 4,910,141 A | 3/1990 | Wong et al. | 536/23.1 |
| 4,913,921 A | 4/1990 | Chaleff et al. | |
| 4,940,835 A | 7/1990 | Shah et al. | |
| 5,057,419 A | 10/1991 | Martin et al. | 435/134 |
| 5,097,093 A | 3/1992 | Vandeventer et al. | 800/200 |
| 5,130,449 A | 7/1992 | Lagarde et al. | 554/186 |
| 5,340,594 A | 8/1994 | Barclay | |
| 5,349,123 A | 9/1994 | Shewmaker et al. | 800/205 |
| 5,376,541 A | 12/1994 | Kawashima et al. | 435/36 |
| 5,405,765 A | 4/1995 | Vasil et al. | 435/172.3 |
| 5,443,974 A | 8/1995 | Hitz et al. | 435/172.3 |
| 5,484,956 A | 1/1996 | Lundquist et al. | 800/205 |
| 5,498,830 A | 3/1996 | Barry et al. | 800/205 |
| 5,552,306 A | 9/1996 | Thomas et al. | 435/134 |
| 5,591,616 A | 1/1997 | Hiei et al. | 435/172.3 |
| 5,614,393 A | 3/1997 | Thomas et al. | 435/134 |
| 5,614,400 A | 3/1997 | Cahoon et al. | 435/172.3 |
| 5,656,319 A | 8/1997 | Barclay | |
| 5,668,292 A | 9/1997 | Somerville et al. | 800/205 |
| 5,668,299 A | 9/1997 | Debonte et al. | 800/230 |
| 5,763,745 A | 6/1998 | Fehr et al. | |
| 5,795,614 A | 8/1998 | Krishnamurthy et al. | |
| 5,880,275 A | 3/1999 | Fischhoff et al. | 536/23.71 |
| 5,886,244 A | 3/1999 | Tomes et al. | 800/205 |
| 5,952,544 A | 9/1999 | Browse et al. | 800/295 |
| 5,959,175 A | 9/1999 | Thomas et al. | 800/287 |
| 5,968,809 A | 10/1999 | Knutzon et al. | 435/254.2 |
| 5,972,664 A | 10/1999 | Knutzon et al. | 435/136 |
| 5,977,436 A | 11/1999 | Thomas et al. | 800/281 |
| 5,985,348 A | 11/1999 | Barclay | |
| 6,051,754 A | 4/2000 | Knutzon | 800/281 |
| 6,075,183 A | 6/2000 | Knutzon | 800/281 |
| 6,117,677 A | 9/2000 | Thompson et al. | 435/410 |
| 6,123,978 A | 9/2000 | Dartey et al. | |
| 6,136,574 A | 10/2000 | Knutzon et al. | 435/134 |
| 6,355,861 B1 | 3/2002 | Thomas | 800/281 |
| 6,384,301 B1 | 5/2002 | Martinell et al. | 800/294 |
| 6,387,883 B1 | 5/2002 | Abbruzzese et al. | |
| 6,399,137 B1 | 6/2002 | Dartey et al. | |
| 6,459,018 B1 | 10/2002 | Knutzon | 800/320.3 |
| 6,506,965 B1* | 1/2003 | Carolo | 800/320.1 |
| 6,603,061 B1 | 8/2003 | Armstrong et al. | 800/294 |
| 6,803,499 B1 | 10/2004 | Anderson et al. | 800/281 |
| 7,037,547 B2 | 5/2006 | Akashe et al. | |
| 7,037,692 B1 | 5/2006 | Thompson et al. | 435/134 |
| 7,041,324 B2 | 5/2006 | Myhre | |
| 7,087,432 B2 | 8/2006 | Qiu et al. | |
| 7,344,747 B2 | 3/2008 | Perlman | |
| 7,550,170 B2 | 6/2009 | Shiiba et al. | |
| 7,554,008 B2 | 6/2009 | Napier et al. | |
| 7,622,632 B2 | 11/2009 | Ursin et al. | 800/281 |
| RE41,139 E | 2/2010 | Knutzon | 800/281 |
| 7,659,120 B2 | 2/2010 | Yadav et al. | |
| 7,705,215 B1 | 4/2010 | Adams et al. | 800/320.1 |
| 7,741,500 B2 | 6/2010 | Arhancet et al. | |
| 7,785,645 B2 | 8/2010 | Siew et al. | |
| 8,057,835 B2 | 11/2011 | Makadia | |
| 8,173,870 B2 | 5/2012 | Ursin | |
| 8,221,819 B2 | 7/2012 | Ursin | |
| 2002/0156254 A1* | 10/2002 | Qiu et al. | 536/23.1 |
| 2003/0082275 A1 | 5/2003 | Myhre | |
| 2004/0107460 A1 | 6/2004 | Fillatti et al. | |
| 2004/0172682 A1 | 9/2004 | Kinney et al. | |
| 2004/0224071 A1 | 11/2004 | Siew et al. | |
| 2005/0132441 A1 | 6/2005 | Damude et al. | 800/281 |
| 2005/0132442 A1 | 6/2005 | Yadav et al. | 800/281 |
| 2005/0181019 A1 | 8/2005 | Palmer et al. | |
| 2005/0244564 A1 | 11/2005 | Perlman | |
| 2006/0062888 A1 | 3/2006 | Shiiba et al. | |
| 2006/0111254 A1 | 5/2006 | Makadia et al. | |
| 2006/0111578 A1 | 5/2006 | Arhancet et al. | |
| 2006/0156435 A1 | 7/2006 | Ursin et al. | 800/281 |
| 2008/0063691 A1 | 3/2008 | Ursin et al. | 800/281 |
| 2008/0155705 A1 | 6/2008 | Zank et al. | |
| 2008/0260929 A1 | 10/2008 | Ursin et al. | |
| 2009/0176879 A1 | 7/2009 | Ursin et al. | 800/281 |
| 2010/0212045 A1 | 8/2010 | Ursin et al. | 800/281 |

FOREIGN PATENT DOCUMENTS

| | | |
|---|---|---|
| EP | 1 086 236 | 6/1999 |
| EP | 0 936 266 A1 | 8/1999 |
| EP | 0 550 162 | 3/2001 |
| EP | 0 644 263 | 12/2002 |
| EP | 0 561 569 | 6/2003 |
| EP | 0 616 644 | 7/2003 |
| EP | 0736 598 | 8/2004 |
| WO | WO 91/10725 A1 | 7/1991 |
| WO | WO 91/13972 | 9/1991 |
| WO | WO 93/06712 | 4/1993 |
| WO | WO 93/11245 | 6/1993 |
| WO | WO 94/11516 | 5/1994 |
| WO | WO 94/18337 | 8/1994 |
| WO | WO 96/10086 | 4/1996 |
| WO | WO 96/21022 | 7/1996 |
| WO | WO 97/21340 | 6/1997 |
| WO | WO 97/30582 | 8/1997 |
| WO | WO 97/46219 | 12/1997 |
| WO | WO 97/46220 | 12/1997 |
| WO | WO 97/46649 A1 | 12/1997 |
| WO | WO 98/45460 | 10/1998 |
| WO | WO 98/46763 | 10/1998 |
| WO | WO 98/46764 A1 | 10/1998 |
| WO | WO 99/64614 | 12/1999 |
| WO | WO 0211550 A2 * | 2/2002 |
| WO | WO 02/092073 | 11/2002 |
| WO | WO 03/075670 | 3/2003 |
| WO | WO 03/072784 | 9/2003 |
| WO | WO 03/099216 | 12/2003 |
| WO | WO 2005/012316 A2 | 2/2005 |
| WO | WO 2005/012316 A3 | 2/2005 |
| WO | WO 2005/021761 | 3/2005 |
| WO | WO 2005/021761 A1 | 3/2005 |
| WO | WO 2005/118814 | 12/2005 |

OTHER PUBLICATIONS

EBI Accession No. AEE85555, dated Feb. 23, 2006.
EBI Accession No. AEE85556, dated Feb. 23, 2006.
GenBank Accession No. AX577009, dated Jan. 8, 2003.
GenPept Accession No. AAF08685, dated Nov. 18, 1999.
"Exciting prospects for stearidonic acid seed oils," *Lipid Technology*, 1996.
"Fats and Oils Formulation," in: Fats and Oils—Formulating and Processing for Applications, O'Brien (Ed.), CRC Press, 2$^{nd}$ Edition, pp. 235-240, 2003.
"Monsanto launches vistive low-linolenic soybeans," *Inform*, 15(11):752 Processing, 2004.
ACS Symposium Series 788, In: Omega-3 Fatty Acids—Chemistry, Nutrition, and Health, Shahidi et al. (Eds.), American Chemical Society, Washington, D.C., pp. 57-3-57-24, 2001.
Aïtzetmüeller et al., "Stearidonic acid (18:4[omega]3) in primula florindae," *Phytochemistry*, 30:4011-4013, 1991.
Fourgoux et al., "Isolation of rapeseed genes expressed early and specifically during development of the male gametophyte," *Plant Mol. Biol.*, 40:857-872, 1999.
Guichardant et al., "Stearidonic acid, and inhibitor of the 5-lipoxygenase pathway. A comparison with timnodonic and dihomogammalinolenic acid," *Lipids*, 28(4):321-24, 1993.
Heppard et al., "Developmental and growth temperature regulation of two different microsomal omega-6 desaturase genes in soybeans," *Plant Physiol.*, 110:311-319, 1996.
James et al., "Metabolism of stearidonic acid in human subjects: comparison with the metabolism of other n-3 fatty acids," *Amer. J. Clin. Nutr.*, 77:1140-1145, 2003.
Kindle et al., "High-frequency nuclear transformation of *Chlamydomonas reinhardtii*," *PNAS USA*, 87:1228-1232, 1990.
Kinney et al., "Manipulating desaturase activities in transgenic crop plants," *Biochem. Soc.*, 30(6):1099-1103, 2002.
Kitamura, "Breeding trials for improving food-processing quality of soybeans," *Trends in Food Sci. & Tech.*, 4:64-67, 1993.

La Guardia et al., "Omega 3 fatty acids: biological activity and effects on human health," *Panminerva Med*, 47(4):245-257, 2005.

Okuley et al., "*Arabidopsis* FAD2 gene encodes the enzyme that is essential for polyunsaturated lipid synthesis," *Plant Cell*, 6:147-158, 1994.

Potrykus, "Gene transfer to plants: assessment of published approaches and results," *Ann. Rev. Plant Physiol. Plant Mol. Biology*, 42:205-225, 1991.

RefSeq Accession No. XP_002166163, dated Jan. 21, 2009.

RefSeq Accession No. XP_374163, dated Aug. 19, 2004.

Rocha-Uribe, "Physical and oxidative stability of mayonnaise enriched with different levels of n-3 fatty acids and stored at different temperatures," 2004 IFT Ann. Meeting, No. 33G13—Nutraceuticals & Functional Foods: Lipid and Probiotic Functional Foods, Las Vegas, NV, Jul. 12-16, 2004.

Sato et al., "Production of y-linolenic acid and stearidonic acid in seeds of marker free transgenic soybean," *Crop Sci.*, 44:646-652, 2004.

Spychalla et al., "Identification of an animal omega-3 fatty acid desaturase by heterologous expression in *Arabidopsis*," *PNAS USA*, 94:1142-1147, 1997.

Whelan et al., "Innovative dietary sources of N-3 fatty acids," *Annu. Rev. Nutr.*, 26:75-103, 2006.

Yadav et al., "Cloning of higher plant omega-3 fatty acid desaturases," *Plant Physiol.*, 103:467-476, 1993.

First Examination Report received in New Zealand Application No. 578165, dated Aug. 11, 2010.

International Search Report and Written Opinion from PCT/US2008/000051, dated Jun. 11, 2008.

Office Action regarding U.S. Appl. No. 10/569,387, dated Oct. 26, 2010.

Score Search Result from U.S. Appl. No. 10/569,387, dated Oct. 20, 2010.

Amendment and Response to Office Action regarding U.S. Appl. No. 10/569,387, dated Jan. 26, 2011.

Final Office Action regarding U.S. Appl. No. 10/569,387, dated Apr. 8, 2011.

Office Action regarding U.S. Appl. No. 11/891,426, dated Feb. 16, 2011.

Office Action regarding U.S. Appl. No. 12/006,388, dated Apr. 27, 2010.

Amendment and Response to Office Action regarding U.S. Appl. No. 12/006,388, dated Jul. 26, 2010.

Final Office Action regarding U.S. Appl. No. 12/006,388, dated Oct. 27, 2010.

Response to Office Action regarding U.S. Appl. No. 12/006,388, dated Jan. 27, 2010.

Advisory Action regarding U.S. Appl. No. 12/006,388, dated Feb. 16, 2011.

Request for Continued Examination regarding U.S. Appl. No. 12/006,388, dated Mar. 18, 2011.

Bhella et al., "Nucleotide sequence of a cDNA from *Limnanthes douglasii* L. encoding a delta-15 linoleic acid desaturase," *Plant Physiol.*, 108:861, 1995.

U.S. Appl. No. 60/089,043, filed Mar. 26, 2007, Knutzon.

U.S. Appl. No. 11/445,506, dated May 31, 2006.

Griffiths et al., "Distribution and Biosynthesis of stearidonic acid in leaves of *Borago officinalis*," *Phytochemistry*, 43(2):381-386, 1996.

Gryson et al., "Detection of DNA during the refining of soybean oil," *JAOCS*, 79(2):171-174, 2002.

Katavic et al., "Alteration of seed fatty acid compositions by an ethyl methanesulfonate-induced mutation in *Arabidopsis thaliana* affecting diacylglycerol acyltransferase activity," *Plant Physiol.*, 108:399-409, 1995.

Kunst et al., "Fatty acid elongation in developing seeds of *Arabidopsis thaliana*," *Plant Physiol. Biochem.*, 30(4):425-434, 1992.

Sayanova et al., "Expression of a borage desaturase cDNA containing an N-terminal cytochrome b5 domain results in the accumulation of high levels of delta6- desaturated fatty acids in transgenic tobacco," *Proc. Natl. Acad. Sci. USA*, 94:4211-4216, 1997.

Tsevegsuren et al., "Gamma-linolenic and stearidonic acid in mongolian boraginaceae seed oils," *J. Amer. Oil Chem. Soc.*, 73:1681-1684, 1996.

Ucciani et al., "Fatty acid composition of oils of saxifragaceae,"*Fiche Technique*, 2(6):491-493, 1995.

Ucciani et al., "Composition en acides gras d'huiles de saxifragaceae,"*Fiche Technique*, 2(6):491-493, 1995.

Ursin et al., "Modification of plant lipids for human health: development of functional land-based omega-3 fatty acids," *J. of Nutrition*, 133(12):4271-4274, 2003.

Office Action regarding U.S. Appl. No. 08/113,561, dated May 13, 2004.

Amendment and Response to Office Action regarding U.S. Appl. No. 08/113,561, dated Oct. 18, 2004.

Final Office Action regarding U.S. Appl. No. 08/113,561, dated Jan. 26, 2005.

Brief on Appeal regarding U.S. Appl. No. 08/113,561, dated Jul. 1, 2005.

Examiner's Answer to Appeal Brief regarding U.S. Appl. No. 08/113,561, dated Sep. 23, 2005.

Reply Brief regarding U.S. Appl. No. 08/113,561, dated Nov. 28, 2005.

Notification of Non-Compliant Appeal Brief regarding U.S. Appl. No. 08/113,561, dated Jun. 26, 2006.

Response to Notification of Non-Compliant Appeal Brief and Supplemental Brief on Appeal regarding U.S. Appl. No. 08/113,561, dated Jul. 24, 2006.

Examiner's Answer to Appeal Brief regarding U.S. Appl. No. 08/113,561, dated Sep. 13, 2006.

Reply Brief regarding U.S. Appl. No. 08/113,561, dated Nov. 13, 2006.

Board of Patent Appeals and Interferences Decision on Appeal regarding U.S. Appl. No. 08/113,561, decided Feb. 20, 2008, dated Feb. 20, 2008.

Transcript of Oral Hearing held Feb. 12, 2008 regarding U.S. Appl. No. 08/113,561, dated Mar. 13, 2008.

Office Action regarding U.S. Appl. No. 08/113,561, dated Mar. 24, 2008.

Response to Office Action regarding U.S. Appl. No. 08/113,561, dated Aug. 25, 2008.

Office Action regarding U.S. Appl. No. 08/113,561, dated Dec. 5, 2008.

Response to Office Action regarding U.S. Appl. No. 08/113,561, dated Mar. 3, 2009.

Final Office Action regarding U.S. Appl. No. 08/113,561, dated Jun. 17, 2009.

Telephonic Interview Summary and Response to Office Action regarding U.S. Appl. No. 08/113,561, dated Sep. 10, 2009.

U.S. Appl. No. 13/551,602, filed Jul. 17, 2012, Ursin.

U.S. Appl. No. 13/551,605, filed Jul. 17, 2012, Ursin.

"Main World Source of Oils," <http://www.cyperlipid.org/glycer/glyc0051.htm>, Jul. 19, 2011, pp. 1-6.

"Silk Soymilk, Made with Soy—One of Nature's Perfect Proteins"; <http://silksoymilk.com/content/silk-difference>; <http://silksoymilk.com/content/how-silk-made>,<http://silksoymilk.com/content/natures-perfect-protein>, Jul. 19, 2011.

Chu et al, "Factors affecting the content of tocopherol in soybean oil," *JAOCS*, 70(12), Dec. 12, 1993; American Oil Chemists Society.

Galiano, "How to make simple southern vanilla ice cream," <www.littlerock.about.com>, Feb. 1, 2002.

The Merck Index—Alpha and Gamma Linolenic Acids, 14th Ed., Merck Research Laboratories, 2006, title page and pp. 954-955.

Sequence alignment of Seq ID No. 3 with U.S. Patent No. 7,554,008—Seq ID No. 1, SCORE search results Oct. 20, 2010; pp. 1-2.

Alonso and Garcia-Maroto, "Plants as 'chemical factories' for the production of polyunsaturated fatty acids," *Biotechnology Advances*, 18(6):481-497, (2000).

Garcia-Maroto et al., "Cloning and molecular characterization of the delta6-desaturase from two echium plant species: production of GLA by heterologous expression in yeast and tobacco," *Lipids*, 37(4):417-26, 2002.

GenBank Accession No. AY234125.

Horrobin, "Fatty acid metabolism in health and disease: the role of delta-6-desaturase[1]," *Am. J. Clin. Nutr.*, 57(Supp.):732S-737S, 1993.

James and Cleland, "Dietary n-3 fatty acids and therapy for reumatoid arthritis," *Semin Arthritis Rheum*, 27(2):85-97, 1997.

Libisch et al., "Chimeras of Delta6-fatty acid and Delta8-sphingolipid desaturases," *Biochem Biophys Res Commun*, 279(3):779-85, 2000.

Meesapyodsuk et al., "Characterization of the regiochemistry and cryptoregiochemistry of a *Caenorhabditis elegans* fatty acid desaturase (FAT-1) expressed in *Saccharomyces cerevisiae*," *Biochemistry*, 39(39):11948-54, 2000.

Michaelson et al., "Functional identification of a fatty acid delta5 desaturase gene from *Caenorhabditis elegans*," *FEBS Lett*, 439(3):215-8, 1998.

Michaelson et al., "Isolation and characterization of a cDNA encoding a Delta8 sphingolipid desaturase from *Aquilegia vulgaris*," *Biochem Soc Trans*, 30(Pt 6):1073-5, 2002.

Napier et al., "A new class of cytochrome b5 fusion proteins," *Biochem J*, 328:717-720, 1997.

Napier et al., "Identification of a *Caenorhabditis elegans* Delta6-fatty-acid-desaturase by heterologous expression in *Saccharomyces cerevisiae*," *Biochem J*, 330(Pt 2):611-4, 1998.

Napier et al., "The role of cytochrome b5 fusion desaturases in the synthesis of polyunsaturated fatty acids," *Prostaglandins Leukot Essent Fatty Acids*, 68(2):135-43, 2003.

Sayanova et al., "Histidine-41 of the cytochrome b5 domain of the borage delta6 fatty acid desaturase is essential for enzyme activity," *Plant Physiol*, 121:641-646, 1999.

Sayanova et al., "Identification of primula fatty acid delta 6-desaturases with n-3 substrate preferences," *FEBS Letters*, 542:100-104, 2003.

Sayanova et al., "$\Delta^6$-unsaturated fatty acids in the species and tissues of the primulaceae," *Phytochemistry*, 52:419-422, 1999.

Shanklin et al., "Eight histidine residues are catalytically essential in a membrane-associated iron enzyme, stearoyl-CoA desaturase, and are conserved in alkane hydroxylase and xylene monooxygenase," *Biochemistry*, 33:12787-12794, 1994.

Sperling and Heinz, "Desaturases fused to their electron donor," *Eur J Lipid Sci Technolo*, 103:158-180, 2001.

Sperling et al., "Functional identification of a delta8-sphingolipid desaturase from *Borago officinalis*," *Arch Biochem Biophys*, 388(2):293-8, 2001.

Whitney et al., "Functional characterisation of two cytochrome b5-fusion desaturases from *Anemone leveillei*: the unexpected identification of a fatty acid Delta6-desaturase," *Planta*, 217(6):983-92, 2003.

"Exciting prospects for stearidonic acid seed oils," *Lipid Technology*, Nov. 1996.

Arondel et al., "Map-based cloning of a gene controlling omega-3 fatty acid desaturation in *Arabidopsis*," *Science*, 258:1353-1355, 1992, Abstract only.

Casas et al., "Transgenic sorghum plants via microprojectile bombardment," *Proc. Natl. Acad. Sci. USA*, 90:11212-11216, 1993.

Covello et al., "Functional expression of the extraplastidial *Arabidopsis thaliana* oleate desaturase gene (FAD2) in *Saccharomyces cerevisiae*," *Plant Physiology*, 111:223-226, 1996.

Fox et al., "Stearoyl-acyl carrier protein delta$^9$ desaturase from *Ricinus communis* is a diiron-oxo protein," *Proc. Natl. Acad. Sci.*, 90:2486-2490, 1993.

Kossmann et al., In: Carbohydrate Bioengineering, "Transgenic plants as a tool to understand starch biosynthesis," Petersen et al. (Eds.), Elsevier Science B.V.; Amsterdam, 1995.

McDonough et al., "Specificity of unsaturated fatty acid-regulated expression of the *Saccharomyces cerevisiae* OLE1 gene," *J. of Biological Chemistry*, 267(9):5931-5936,1992.

Post-Beittenmiller et al., "Expression of holo and Apo forms of spinach acyl carrier protein-I in leaves of transgenic tobacco plants," *The Plant Cell*, 1:889-899, 1989.

Reddy et al., "Expression of a cyanobacterial delta$^6$-desaturase gene results in y-linolenic acid production in transgenic plants," *Nature Biotechnology*, 14:639-642, 1996.

Reddy et al., "Isolation of a delta 6-desaturase gene from the *Cyanobacterium synechocystis* sp. strain PCC 6803 by gain-of-function expression *Anabaena* sp. strain PCC 7120," *Plant Mol. Biol.*, 22(2):293-300, 1993, Abstract only.

Stephanopoulos et al., "Metabolic engineering—methodologies and future prospects," *Trends in Biotechnology*, 11:392-396. 1993.

* cited by examiner

EXPRESSION OF FATTY ACID DESATURASES IN CORN

This application is a national stage application under 35 U.S.C. §371 of International Application No. PCT/US2005/012778 filed Apr. 15, 2005, which claims the priority of U.S. Provisional Patent Application Ser. No. 60/563,135, filed Apr. 16, 2004, the entire disclosures of which are each specifically incorporated herein by reference.

BACKGROUND OF THE INVENTION

1. Field of the Invention

The invention relates generally to expression of desaturase enzymes that modulate the number and location of double bonds in long chain poly-unsaturated fatty acids (LC-PUFA's) in corn and compositions derived therefrom.

2. Description of the Related Art

The primary products of fatty acid biosynthesis in most organisms are 16- and 18-carbon compounds. The relative ratio of chain lengths and degree of unsaturation of these fatty acids vary widely among species. Mammals, for example, produce primarily saturated and monounsaturated fatty acids, while most higher plants produce fatty acids with one, two, or three double bonds, the latter two comprising polyunsaturated fatty acids (PUFA's).

Two main families of PUFAs are the omega-3 fatty acids (also represented as "n-3" fatty acids), exemplified by eicosapentaenoic acid (EPA, 20:4, n-3), and the omega-6 fatty acids (also represented as "n-6" fatty acids), exemplified by arachidonic acid (ARA, 20:4, n-6). PUFAs are important components of the plasma membrane of the cell and adipose tissue, where they may be found in such forms as phospholipids and as triglycerides, respectively. PUFAs are necessary for proper development in mammals, particularly in the developing infant brain, and for tissue formation and repair.

Several disorders respond to treatment with fatty acids. Supplementation with PUFAs has been shown to reduce the rate of restenosis after angioplasty. The health benefits of certain dietary omega-3 fatty acids for cardiovascular disease and rheumatoid arthritis also have been well documented (Simopoulos, 1997; James et al., 2000). Further, PUFAs have been suggested for use in treatments for asthma and psoriasis. Evidence indicates that PUFAs may be involved in calcium metabolism, suggesting that PUFAs may be useful in the treatment or prevention of osteoporosis and of kidney or urinary tract stones. The majority of evidence for health benefits applies to the long chain omega-3 fats, EPA and docosahexanenoic acid (DHA, 22:6), which are in fish and fish oil. With this base of evidence, health authorities and nutritionists in Canada (Scientific Review Committee, 1990, Nutrition Recommendations, Minister of National Health and Welfare, Canada, Ottawa), Europe (de Deckerer et al., 1998), the United Kingdom (The British Nutrition Foundation, 1992, Unsaturated fatty-acids—nutritional and physiological significance: The report of the British Nutrition Foundation's Task Force, Chapman and Hall, London), and the United States (Simopoulos et al., 1999) have recommended increased dietary consumption of these PUFAs.

PUFAs also can be used to treat diabetes (U.S. Pat. No. 4,826,877; Horrobin et al, 1993). Altered fatty acid metabolism and composition have been demonstrated in diabetic animals. These alterations have been suggested to be involved in some of the long-term complications resulting from diabetes, including retinopathy, neuropathy, nephropathy and reproductive system damage. Primrose oil, which contains γ-linolenic acid (GLA, 18:3, Δ6, 9, 12), has been shown to prevent and reverse diabetic nerve damage.

PUFAs, such as linoleic acid (LA, 18:2, Δ9, 12) and α-linolenic acid (ALA, 18:3, Δ9, 12, 15), are regarded as essential fatty acids in the diet because mammals lack the ability to synthesize these acids. However, when ingested, mammals have the ability to metabolize LA and ALA to form the n-6 and n-3 families of long-chain polyunsaturated fatty acids (LC-PUFA). These LC-PUFA's are important cellular components conferring fluidity to membranes and functioning as precursors of biologically active eicosanoids such as prostaglandins, prostacyclins, and leukotrienes, which regulate normal physiological functions. Arachidonic acid is the principal precursor for the synthesis of eicosanoids, which include leukotrienes, prostaglandins, and thromboxanes, and which also play a role in the inflammation process. Administration of an omega-3 fatty acid, such as SDA, has been shown to inhibit biosynthesis of leukotrienes (U.S. Pat. No. 5,158,975). The consumption of SDA has been shown to lead to a decrease in blood levels of proinflammatory cytokines TNF-α and IL-1, (U.S. Publication. No. 20040039058).

In mammals, the formation of LC-PUFA is rate-limited by the step of Δ6 desaturation, which converts LA to γ-linolenic acid (GLA, 18:3, Δ6, 9, 12) and ALA to SDA (18:4, Δ6, 9, 12, 15). Many physiological and pathological conditions have been shown to depress this metabolic step even further, and consequently, the production of LC-PUFA. To overcome the rate-limiting step and increase tissue levels of EPA, one could consume large amounts of ALA. However, consumption of just moderate amounts of SDA provides an efficient source of EPA, as SDA is about four times more efficient than ALA at elevating tissue EPA levels in humans (U.S. Publication. No. 20040039058). In the same studies, SDA administration was also able to increase the tissue levels of docosapentaenoic acid (DPA), which is an elongation product of EPA. Alternatively, bypassing the Δ6-desaturation via dietary supplementation with EPA or DHA can effectively alleviate many pathological diseases associated with low levels of PUFA. However, as set forth in more detail below, currently available sources of PUFA are not desirable for a multitude of reasons. The need for a reliable and economical source of PUFA's has spurred interest in alternative sources of PUFA's.

Major long chain PUFAs of importance include DHA and EPA, which are primarily found in different types of fish oil, and ARA, found in filamentous fungi such as *Mortierella*. For DHA, a number of sources exist for commercial production including a variety of marine organisms, oils obtained from coldwater marine fish and egg yolk fractions. Commercial sources of SDA include the plant genera *Trichodesma*, *Borago* (borage) and *Echium*. However, there are several disadvantages associated with commercial production of PUFAs from natural sources. Natural sources of PUFAs, such as animals and plants, tend to have highly heterogeneous oil compositions. The oils obtained from these sources therefore can require extensive purification to separate out one or more desired PUFAs or to produce an oil which is enriched in one or more PUFAs.

Natural sources of PUFAs also are subject to uncontrollable fluctuations in availability. Fish stocks may undergo natural variation or may be depleted by overfishing. In addition, even with overwhelming evidence of their therapeutic benefits, dietary recommendations regarding omega-3 fatty acids are not heeded. Fish oils have unpleasant tastes and odors, which may be impossible to economically separate from the desired product, and can render such products unacceptable as food supplements. Animal oils, and particularly fish oils, can accumulate environmental pollutants. Foods may be enriched with fish oils, but again, such enrichment is problematic because of cost and declining fish stocks worldwide. This problem is also an impediment to consumption and intake of whole fish. Nonetheless, if the health messages to increase fish intake were embraced by communities, there would likely be a problem in meeting demand for fish. Furthermore, there are problems with sustainability of this industry, which relies heavily on wild fish stocks for aquaculture feed (Naylor et al., 2000).

Other natural limitations favor a novel approach for the production of omega-3 fatty acids. Weather and disease can cause fluctuation in yields from both fish and plant sources. Cropland available for production of alternate oil-producing crops is subject to competition from the steady expansion of human populations and the associated increased need for food production on the remaining arable land. Crops that do produce PUFAs, such as borage, have not been adapted to commercial growth and may not perform well in monoculture. Growth of such crops is thus not economically competitive where more profitable and better-established crops can be grown. Large-scale fermentation of organisms such as *Mortierella* is also expensive. Natural animal tissues contain low amounts of ARA and are difficult to process. Microorganisms such as *Porphyridium* and *Mortierella* are difficult to cultivate on a commercial scale.

A number of enzymes are involved in the biosynthesis of PUFAs. LA (18:2, Δ9, 12) is produced from oleic acid (OA, 18:1, Δ9) by a Δ12 desaturase while ALA (18:3, Δ9, 12, 15) is produced from LA by a Δ15 desaturase. SDA (18:4, Δ6, 9, 12, 15) and GLA (18:3, Δ6, 9, 12) are produced from LA and ALA by a Δ6 desaturase. However, as stated above, mammals cannot desaturate beyond the Δ9 position and therefore cannot convert oleic acid into LA. Likewise, ALA cannot be synthesized by mammals. Other eukaryotes, including fungi and plants, have enzymes which desaturate at the carbon 12 and carbon 15 positions. The major polyunsaturated fatty acids of animals therefore are derived from diet via the subsequent desaturation and elongation of dietary LA and ALA.

Various genes encoding desaturases have been described. For example, U.S. Pat. No. 5,952,544 describes nucleic acid fragments isolated and cloned from *Brassica napus* that encode fatty acid desaturase enzymes. Expression of the nucleic acid fragments of the '544 patent resulted in accumulation of ALA. However, in transgenic plants expressing the *B. napus* Δ15 desaturase, substantial LA remains unconverted by the desaturase. It has been demonstrated that certain fungal Δ15 desaturases are capable of converting LA to ALA when expressed in plants. In particular, fungal Δ15 desaturases from *Neurospora crassa* and *Aspergillus* (*Emericella*) *nidulans* have been effective (International Publication No. WO 03/099216, incorporated herein by reference). Increased ALA levels allow a Δ6 desaturase, when co-expressed with a nucleic acid encoding for the Δ15 desaturase, to act upon the ALA, thereby producing greater levels of SDA. Because of the multitude of beneficial uses for SDA, there is a need to create a substantial increase in the yield of SDA.

Nucleic acids from various sources have been sought for use in increasing SDA yield. Genes encoding Δ6 desaturases have been isolated from the fungus *Mortierella alpina* (U.S. Pat. No. 6,075,183) and the plant *Primula* (International Publication No. WO 05/021761, incorporated herein by reference). These have been shown to be able to convert ALA to SDA in yeast and plants.

Therefore, it would be advantageous to obtain genetic material involved in PUFA biosynthesis and to express the isolated material in a plant system, in particular, a land-based terrestrial crop plant system, which can be manipulated to provide production of commercial quantities of one or more PUFA's. There is also a need to increase omega-3 fat intake in humans and animals. Thus there is a need to provide a wide range of omega-3 enriched foods and food supplements so that subjects can choose feed, feed ingredients, food and food ingredients which suit their usual dietary habits. Particularly advantageous would be seed oils and meal with increased SDA.

Currently there is only one omega-3 fatty acid, ALA, available in vegetable oils. However, there is poor conversion of ingested ALA to the longer-chain omega-3 fatty acids such as EPA and DHA. It has been demonstrated in copending U.S. Publication. No. 20040039058 for "Treatment And Prevention Of Inflammatory Disorders," that elevating ALA intake from the community average of 1/g day to 14 g/day by use of flaxseed oil only modestly increased plasma phospholipid EPA levels. A 14-fold increase in ALA intake resulted in a 2-fold increase in plasma phospholipid EPA (Manzioris et al., 1994). Thus, to that end, there is a need for efficient and commercially viable production of PUFAs using fatty acid desaturases, genes encoding them, and recombinant methods of producing them. A need also exists for oils containing higher relative proportions of specific PUFAs, and food and feed compositions and supplements containing them. A need also exists for reliable economical methods of producing specific PUFA's.

Despite inefficiencies and low yields as described above, the production of omega-3 fatty acids via the terrestrial food chain is an enterprise beneficial to public health and, in particular, the production of SDA. SDA is important because, as described above, there is low conversion of ALA to EPA. This is because the initial enzyme in the conversion, Δ6-desaturase, has low activity in humans and is rate-limiting. Evidence that Δ6-desaturase is rate-limiting is provided by studies which demonstrate that the conversion of its substrate, ALA, is less efficient than the conversion of its product, SDA to EPA in mice and rats (Yamazaki et al., 1992; Huang, 1991).

Certain seed oils such as corn lack SDA or other important omega-3 fatty acids altogether and thus there is a great need in the art for plants comprising seed oil with improved PUFA profiles. Such oils can be utilized to produce foods and food supplements enriched in omega-3 fatty acids and consumption of such foods effectively increases tissue levels of EPA. Foods and food stuffs, such as milk, margarine and sausages, all made or prepared with omega-3 enriched oils, will result in health benefits. Animal feedstocks containing the extracted oil or meal or full-fat grain enriched in omega-3 fatty acids can also be used to effectively increase tissue levels of EPA and provide health benefits for the livestock as well as productivity. Thus, there exists a strong need for novel plants expression desaturases for the creation of oils enriched in PUFAs.

SUMMARY OF THE INVENTION

In one aspect, the invention provides an endogenous corn seed oil containing stearidonic acid. In certain embodiments of the invention, the corn seed oil comprises from about 0.1% to about 33% stearidonic acid and in further embodiments may comprise from about 5% to about 15%; from about 5% to about 10%; from about 7.5% to about 12%; from about 10% to about 15%; about 12% to about 15%, from about 10% to about 33%, from about 15% to about 33%, from about 15% to about 32%, from about 20% to about 33%, from about 20% to about 30%, from about 25% to about 30% and from about 25% to about 33% stearidonic acid, including all intermediate values as well as those shown in the Tables below. An endogenous corn seed oil provided by the invention may further comprise gamma-linolenic acid. In certain embodiments of the invention, the gamma-linolenic acid content of the oil may be from about 0.01% to about 7.5% and from about 0.01% to about 5%, including less than about 5% and less than about 3% and specifically including all intermediate values and those shown in the Tables below. In certain embodiments of the invention, α-linolenic acid content may be less than about 5, 10, 15 or 20%.

In further embodiments of the invention, a corn seed oil of the invention may comprise a ratio of stearidonic acid to gamma-linolenic acid of from about 1:1 to about 10:1, from about 2:1 to about 10:1, from about 3:1 to about 5:1 or at least about 3:1. A corn seed oil provided by the invention may further comprise a ratio of omega-3 to omega-6 fatty acids of from about 0.5%: 1 to about 10:1, from about 5:1 to about 10:1, and at least about 5:1.

Another aspect of the invention provides a method of producing corn seed oil containing a modified PUFA profile comprising the steps of (a) obtaining seeds of a plant according to the invention; and (b) extracting the oil from said seeds. Preferred methods of transforming such plant cells in certain embodiments of the invention include the use of Ti and Ri plasmids of *Agrobacterium*, electroporation, and high-velocity ballistic bombardment.

In still another aspect, the invention provides a method of producing a corn plant comprising seed oil containing altered levels of omega-3 fatty acids comprising introducing a recombinant vector of the invention into an oil-producing plant. In the method, introducing the recombinant vector may comprise genetic transformation. In one embodiment, transformation comprises the steps of: (a) transforming a plant cell with a recombinant vector of the invention; and (b) regenerating the plant from the plant cell, wherein the plant has altered levels of omega-3 fatty acids relative to a corresponding plant of the same genotype that was not transformed with the vector. The plant may be further defined as transformed with a nucleic acid sequence encoding a polypeptide having desaturase activity that desaturates a fatty acid molecule at carbon 12 and/or 15. The plant may comprise increased SDA and GLA. The method may further comprise introducing the recombinant vector into a plurality of corn plants and screening the plants or progeny thereof having inherited the recombinant vector for a plant having a desired profile of omega-3 fatty acids.

In still yet another aspect, the invention provides a method of increasing the nutritional value of an edible product for human or animal consumption, comprising adding a corn seed oil provided by the invention to the edible product. In certain embodiments, the product is human and/or animal food. The edible product may also be animal feed and/or a food supplement. In the method, the oil may increase the SDA content of the edible product and/or may increase the ratio of omega-3 to omega-6 fatty acids of the edible product. The edible product may lack SDA prior to adding the oil.

In still yet another aspect, the invention provides a method of manufacturing food or feed, comprising adding a corn seed oil provided by the invention to starting food or feed ingredients to produce the food or feed. In certain embodiments, the method is further defined as a method of manufacturing food and/or feed. The invention also provides food or feed made by the method.

In still yet another aspect, the invention comprises a method of providing SDA to a human or animal, comprising administering a seed oil of the invention to said human or animal. In the method, the seed oil may be administered in an edible composition, including food or feed. Examples of food include beverages, infused foods, sauces, condiments, salad dressings, fruit juices, syrups, desserts, icings and fillings, soft frozen products, confections or intermediate food. The edible composition may be substantially a liquid or solid. The edible composition may also be a food supplement and/or nutraceutical. In the method, the seed oil may be administered to a human and/or an animal. Examples of animals the oil may be administered to include livestock or poultry.

In yet another aspect, a corn seed oil of the invention may be obtained from a plant transformed with isolated nucleic acids encoding a polypeptide capable of desaturating a fatty acid molecule at carbon 6 (Δ6-desaturase). In one embodiment, an isolated polynucleotide sequence isolated from a *Primula* species having unique desaturase activity may be used. In certain embodiments, the isolated polynucleotides are isolated, for example, from *Primula juliae*. In certain further embodiments of the invention, the polynucleotides encode a polypeptide having at least 90% homology to the polypeptide sequence of SEQ ID NO:3 and/or SEQ ID NO:4, including at least about 92%, 95%, 98% and 99% homology to these sequences. Such sequences may have substrate specificity for α-linolenic acid relative to linoleic acid. In certain embodiments, there is at least 2:1 substrate specificity for α-linolenic acid relative to linoleic acid, including from about 2:1 to about 2.9:1.

In another aspect, a corn plant is transformed with an isolated polynucleotide that encodes a polypeptide having desaturase activity that desaturates a fatty acid molecule at carbon 6, comprising a sequence selected from the group consisting of: (a) a polynucleotide encoding the polypeptide of SEQ ID NO:3 or SEQ ID NO:4; (b) a polynucleotide comprising the nucleic acid sequence of SEQ ID NO:1 or SEQ ID NO:2; and (c) a polynucleotide hybridizing to SEQ II) NO:1 or SEQ ID NO:2, or a complement thereof, under conditions of 5×SSC, 50% formamide and 42° C.

In yet another aspect, the invention provides an isolated polynucleotide selected from the group consisting of: (a) a polynucleotide comprising the nucleic acid sequence of SEQ ID NO:8; (b) a polynucleotide hybridizing to SEQ ID NO:8 under conditions of 5×SSC, 50% formamide and 42° C., wherein the polynucleotide encodes a polypeptide having desaturase activity that desaturates a fatty acid molecule at carbon 6; and (c) a polynucleotide having at least 90% sequence identity to the nucleic acid sequence of SEQ ID NO:8, wherein the polynucleotide encodes a polypeptide having desaturase activity that desaturates a fatty acid molecule at carbon 6; and (d) a complement of the sequence of (a), (b), or (c). In one embodiment, such a polynucleotide may comprise the nucleic acid sequence of SEQ ID NO:9. Further provided by the invention are recombinant constructs and transgenic plants comprising such polynucleotides, as well as the seed oil produced by the plants.

In yet another aspect, a corn plant is transformed with a recombinant vector comprising an isolated polynucleotide in accordance with the invention. The term "recombinant vector" as used herein, includes any recombinant segment of DNA that one desires to introduce into a host cell, tissue and/or organism, and specifically includes expression cassettes isolated from a starting polynucleotide. A recombinant vector may be linear or circular. In various aspects, a recombinant vector may comprise at least one additional sequence chosen from the group consisting of: regulatory sequences operatively coupled to the polynucleotide; selection markers operatively coupled to the polynucleotide; marker sequences operatively coupled to the polynucleotide; a purification moiety operatively coupled to the polynucleotide; and a targeting sequence operatively coupled to the polynucleotide.

In still yet another aspect, the invention provides corn cells transformed with the polynucleotides described herein. In a further embodiment, the cells are transformed with recombinant vectors containing constitutive and tissue-specific promoters in addition to the polynucleotides. In certain embodiments of the invention, such cells may be further defined as transformed with a nucleic acid sequence encoding a polypeptide having desaturase activity that desaturates a fatty acid molecule at carbon 12 and/or 15.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein. The invention can be more fully understood from the following description of the figures.

DETAILED DESCRIPTION OF THE INVENTION

Figure 1:
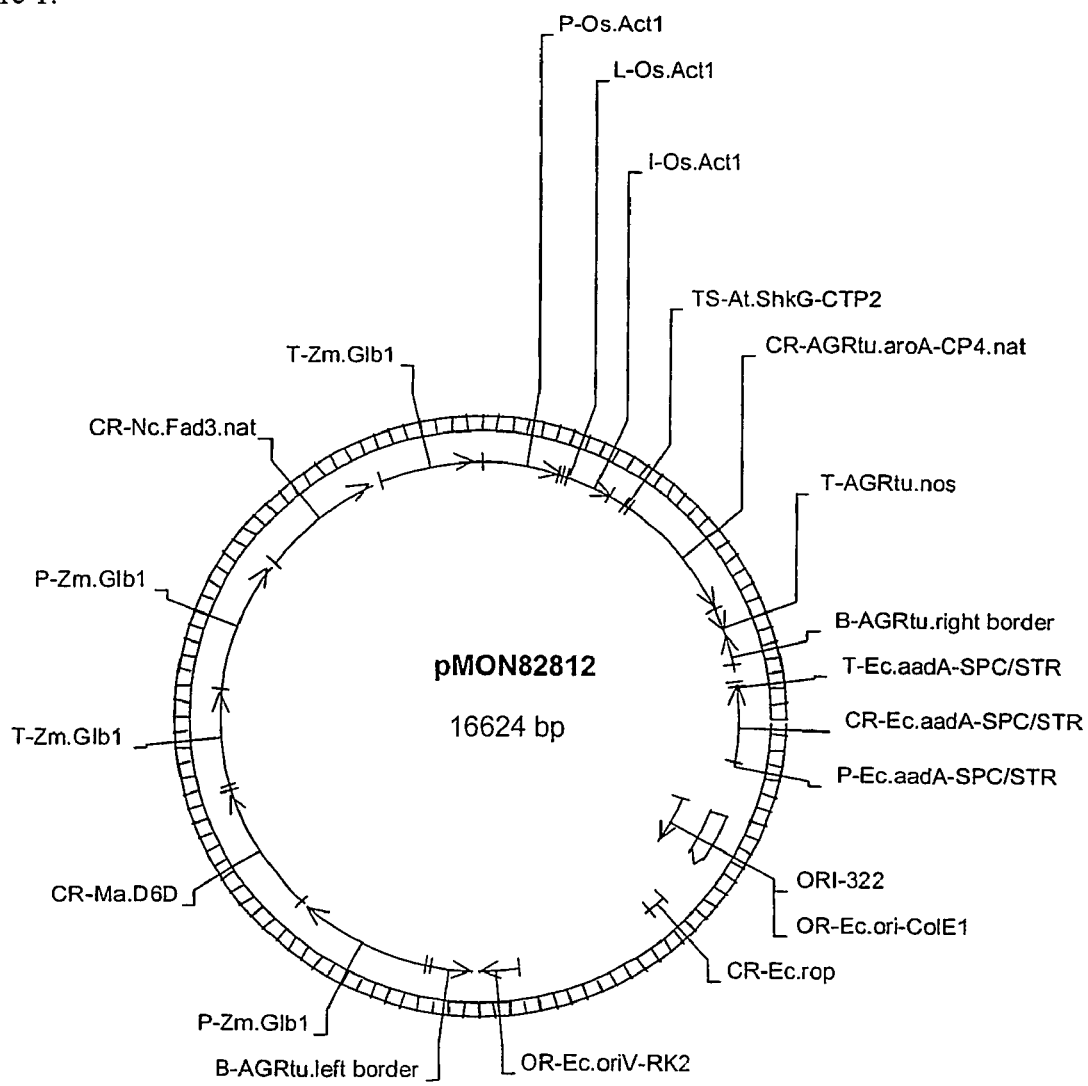
FIG. 1 shows a map of vector pMON82812.

The invention overcomes the limitations of the prior art by providing methods and compositions for creation of plants with improved PUFA content and the seed oils produced thereby. In one embodiment of the invention, Applicants have provided transgenic corn (Zea inays) plants that produce an endogenous corn seed oil containing stearidonic acid (SDA) and may also comprise γ-linolenic acid (GLA). This is significant because corn seed oil normally lacks these components, each of which have been shown to have important health benefits. The corn seed oil is endogenous in that it may be produced by a corn seed without the need for external addition of, for example, SDA. Such an endogenous oil may be an extracted oil composition that can be used as a food and feed ingredient and thereby benefit human or animal health. The modification of fatty acid content of an organism such as a plant thus presents many benefits such as improved nutrition and health benefits. Modification of fatty acid content can be used in accordance with the invention to achieve beneficial levels or profiles of desired PUFA's in plants such as corn, plant parts, and plant products, including plant seed oils. For example, when the desired PUFA's are produced in the seed tissue of a plant, the oil may be isolated from the seeds typically resulting in an oil high in desired PUFAs or an oil having a desired fatty acid content or profile, which may in turn be used to provide beneficial characteristics in food stuffs and other products. The invention in particular provides endogenous corn seed oil having SDA.

Various aspects of the invention include methods and compositions for modification of PUFA content of a cell, for example, modification of the PUFA content of a corn plant cell. Compositions related to the invention include novel isolated polynucleotide sequences and polynucleotide constructs introduced into plants and/or plant parts. An example of such an isolated polynucleotide is a *Primula* fatty acid desaturase such as a *Primula* Δ6-desaturase. Corn cells prepared in accordance with the invention may comprise other fatty acid desaturases, including known Δ6 desaturases such as that from *Mortierella alpina*. The inventors have shown in particular that expression of different Δ6 and Δ15 fatty acid desaturases yields corn seed oil containing SDA. Certain embodiments of the invention therefore provide corn plants and cells transformed with coding sequences of Δ6 and Δ15 fatty acid desaturases. In one embodiment of the invention, a Δ15-desaturase may be from a fungal source, including *Neurospora crassa* and *Aspergillus nidulans*. Various embodiments of the invention may use combinations of desaturase polynucleotides and the encoded polypeptides that typically depend upon the host cell, the availability of substrate(s), and the desired end product(s). "Desaturase" refers to a polypeptide that can desaturate or catalyze formation of a double bond between consecutive carbons of one or more fatty acids to produce a mono- or poly-unsaturated fatty acid or precursor thereof. Of particular interest are polypeptides that can catalyze the conversion of oleic acid to LA, LA to ALA, or ALA to SDA, which includes enzymes which desaturate at the 12, 15, or 6 positions. The term "polypeptide" refers to any chain of amino acids, regardless of length or post-translational modification (e.g., glycosylation or phosphorylation). Considerations for choosing a specific polypeptide having desaturase activity include, but are not limited to, the pH optimum of the polypeptide, whether the polypeptide is a rate limiting enzyme or a component thereof, whether the desaturase used is essential for synthesis of a desired PUFA, and/or whether a co-factor is required by the polypeptide. The expressed polypeptide preferably has characteristics that are compatible with the biochemical environment of its location in the host cell. For example, the polypeptide may have to compete for substrate(s).

Analyses of the $K_m$ and specific activity of a polypeptide in question may be considered in determining the suitability of a given polypeptide for modifying PUFA(s) production, level, or profile in a given host cell. The polypeptide used in a particular situation is one which typically can function under the conditions present in the intended host cell, but otherwise may be any desaturase polypeptide having a desired characteristic or being capable of modifying the relative production, level or profile of a desired PUFA(s) or any other desired characteristics as discussed herein. The substrate(s) for the expressed enzyme may be produced by the host cell or may be exogenously supplied. To achieve expression, the polypeptide(s) of the instant invention are encoded by polynucleotides as described below.

In another aspect of the invention, vectors containing a nucleic acid, or fragment thereof, may be used containing a promoter, a desaturase coding sequence and a termination region for transfer into an organism in which the promoter and termination regions are functional. Accordingly, corn plants producing recombinant Δ6-desaturase are provided by this invention. An example of such a Δ6-desaturase coding sequence provided by the invention that has been optimized for expression in corn is given by SEQ ID NO:8 and SEQ ID NO:9. The invention therefore specifically provides nucleic acids comprising this sequence, as well as sequences having at least 90% sequence identity with these sequences, including at least 93%, 95%, 98% and 99% identity. Polypeptide or polyiiucleotide comparisons may be carried out and identity determined using sequence analysis software, for example, the Sequence Analysis software package of the GCG Wisconsin Package (Accelrys, San Diego, Calif.), MEGAlign (DNAStar, Inc., 1228 S. Park St., Madison, Wis. 53715), and MacVector (Oxford Molecular Group, 2105 S. Bascom Avenue, Suite 200, Campbell, Calif. 95008). Such software matches similar sequences by assigning degrees of similarity or identity.

Nucleic acid constructs may be provided that integrate into the genome of a host cell or are autonomously replicated (e.g., episomally replicated) in the host cell. For production of ALA and/or SDA, the expression cassettes (i.e., a polynucleotide encoding a protein that is operatively linked to nucleic acid sequence(s) that directs the expression of the polynucleotide) generally used include an expression cassette which provides for expression of a polynucleotide encoding a Δ6- and/or Δ15-desaturase. In certain embodiments a host cell may have wild type oleic acid content.

Methods and compositions for the construction of expression vectors, when taken in light of the teachings provided herein, for expression of desaturase enzymes will be apparent to one of ordinary skill in the art. Expression vectors, as described herein, are DNA or RNA molecules engineered for controlled expression of a desired polynucleotide, e.g., the desaturase-encoding polynucleotide. Examples of vectors include plasmids, bacteriophages, cosmids or viruses. Shuttle vectors, e.g. (Wolk et al. 1984; Bustos et al., 1991) are also contemplated in accordance with the present invention. Reviews of vectors and methods of preparing and using them can be found in Sambrook et al. (2001); Goeddel (1990); and Perbal (1988). Sequence elements capable of effecting expression of a polynucleotide include promoters, enhancer elements, upstream activating sequences, transcription termination signals and polyadenylation sites.

Polynucleotides encoding desaturases may be placed under transcriptional control of a strong promoter. In some cases this leads to an increase in the amount of desaturase enzyme expressed and concomitantly an increase in the fatty acid produced as a result of the reaction catalyzed by the enzyme. Examples of such promoters include the 35S CaMV (cauliflower mosaic virus), 34S FMV (figwort mosaic virus) (see, e.g., U.S. Pat. No. 5,378,619, the contents of which are herein incorporated in their entirety) and Lec (from corn). There are a wide variety of plant promoter sequences which may be used to drive tissue-specific expression of polynucleotides encoding desaturases in transgenic plants. Indeed, in particular embodiments of the invention, the promoter used is a seed specific promoter. Examples of promoters that way be used in this regard include the 5' regulatory regions from such genes as napin, which are regulated during plant seed maturation (Kridl et al., *Seed Sci. Res.* 1:209:219, 1991), phaseolin (Bustos, et al., *Plant Cell,* 1(9):839-853, 1989), soybean trypsin inhibitor (Riggs, et al., *Plant Cell* 1(6):609-621, 1989), ACP (Baerson et al., *Plant Mol. Biol.,* 22(2):255-267, 1993), stearoyl-ACP desaturase (Slocombe et al., *Plant Physiol.* 104(4):167-176, 1994), soybean α' subunit of β-conglycinin (P-Gm7S, see for example, Chen et al., *Proc. Natl. Acad. Sci.* 83:8560-8564, 1986), *Vicia faba* USP (P-Vf.Usp, see for example, SEQ ID NO:1, 2, and 3, U.S. patent application Ser. No. 10/429,516), the globulin promoter (see for example Belanger and Kriz, *Genet.* 129: 863-872 (1991), soybean alpha subunit of β-conglycinin (7S alpha) (U.S. patent application Ser. No. 10/235,618, incorporated by reference) barley seed peroxidin PER1 promoter (see for example, Stacey et al., *Plant Mol. Biol.,* 31:1205-1216, 1996), and Zea mays L3 oleosin promoter (P-Zm.L3, see, for example, Hong et al., *Plant Mol. Biol.,* 34(3):549-555, 1997; see also U.S. Pat. No. 6,433,252, the disclosure of which is specifically incorporated herein by reference).

Examples of promoters highly expressed in the endosperm include promoters from genes encoding zeins, which are a group of storage proteins found in maize endosperm. Genomic clones for zein genes have been isolated (Pedersen et al., *Cell* 29:1015-1026 (1982), and Russell et al., *Transgenic Res.* 6(2):157-168) and the promoters from these clones, including the 15 kD, 16 kD, 19 kD, 22 kD, and 27 kD genes, could also be used to provide expression in the endosperm in accordance with the invention (see, e.g., U.S. Pat. No. 6,326,527, specifically incorporated herein by reference in the entirety). Other suitable promoters known to function in maize, and in other plants, include the promoters for the following genes: waxy (granule bound starch synthase), Brittle and Shrunken 2 (ADP glucose pryophosphorylase), Shrunken 1 (sucrose synthase), branching enzymes I and II, starch synthases, debranching enzymes, oleosins, glutelins, sucrose synthases (Yang et al., 1990), Betl1 (basal endosperm transfer layer) and globulin1. Other promoters useful in the practice of the invention that are known by one of skill in the art are also contemplated by the invention.

The ordinarily skilled artisan can determine vectors and regulatory elements (including operably linked promoters and coding regions) suitable for expression in a particular host cell. "Operably linked" in this context means that the promoter and terminator sequences effectively function to regulate transcription. As a further example, a vector appropriate for expression of Δ6 and/or Δ15 desaturase in transgenic corn plants can comprise a seed-specific promoter sequences operably linked to the desaturase coding region and further operably linked to a seed storage protein termination signal or the nopaline synthase termination signal. As a still further example, a vector for use in expression of desaturases in plants can comprise a constitutive promoter or a tissue specific promoter operably linked to the desaturase coding region and further operably linked to a constitutive or tissue specific terminator or the nopaline synthase termination signal.

Modifications of the nucleotide sequences or regulatory elements disclosed herein which maintain the functions contemplated herein are within the scope of this invention. Such modifications include insertions, substitutions and deletions, and specifically substitutions which reflect the degeneracy of the genetic code.

Standard techniques for the construction of such recombinant vectors are well-known to those of ordinary skill in the art and can be found in references such as Sambrook et al. (2001), or any of the myriad of laboratory manuals on recombinant DNA technology that are widely available. A variety of strategies are available for ligating fragments of DNA, the choice of which depends on the nature of the termini of the DNA fragments. It is further contemplated in accordance with the present invention to include in a nucleic acid vector other nucleotide sequence elements which facilitate cloning, expression or processing, for example sequences encoding signal peptides, a sequence encoding KDEL, which is required for retention of proteins in the endoplasmic reticulum or sequences encoding transit peptides which direct Δ6-desaturase to the chloroplast. Such sequences are known to one of ordinary skill in the art. An optimized transit peptide is described, for example, by Van den Broeck et al. (1985). Prokaryotic and eukaryotic signal sequences are disclosed, for example, by Michaelis et al. (1982).

Once the desired genomic or cDNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA also can be employed.

Some or all of the coding sequence for a polypeptide having desaturase activity may be from a natural source. In some situations, however, it is desirable to modify all or a portion of the codons, for example, to enhance expression, by employing host preferred codons. Host-preferred codons can be determined from the codons of highest frequency in the proteins expressed in the largest amount in a particular host species and/or tissue of interest. Thus, the coding sequence for a polypeptide having desaturase activity can be synthesized in whole or in part. All or portions of the DNA also can be synthesized to remove any destabilizing sequences or regions of secondary structure which would be present in the transcribed mRNA. All or portions of the DNA also can be synthesized to alter the base composition to one more preferable in the desired host cell. Methods for synthesizing sequences and bringing sequences together are well established in the literature. In vitro mutagenesis and selection, site-directed mutagenesis, or other means can be employed to obtain mutations of naturally-occurring desaturase genes to produce a polypeptide having desaturase activity in vivo with more desirable physical and kinetic parameters for function in the host cell, such as a longer half-life or a higher rate of production of a desired polyunsaturated fatty acid.

Once the polynucleotide encoding a desaturase polypeptide has been obtained, it is placed in a vector capable of replication in a host cell, or is propagated in vivo by means of techniques such as PCR or long PCR. Replicating vectors can include plasmids, phage, viruses, cosmids and the like. Desirable vectors include those useful for mutagenesis of the gene of interest or for expression of the gene of interest in host cells. The technique of long PCR has made in vitro propagation of large constructs possible, so that modifications to the gene of interest, such as mutagenesis or addition of expression signals, and propagation of the resulting constructs can occur entirely in vitro without the use of a replicating vector or a host cell.

For expression of a desaturase polypeptide, functional transcriptional and translational initiation and termination regions are operably linked to the polynucleotide encoding the desaturase polypeptide. Expression of the polypeptide coding region can take place in vitro or in a host cell. Transcriptional and translational initiation and termination regions are derived from a variety of nonexclusive sources, including the polynucleotide to be expressed, genes known or suspected to be capable of expression in the desired system, expression vectors, chemical synthesis, or from an endogenous locus in a host cell.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When increased expression of the desaturase polypeptide in the source organism is desired, several methods can be employed. Additional genes encoding the desaturase polypeptide can be introduced into the host organism. Expression from the native desaturase locus also can be increased through homologous recombination, for example by inserting a stronger promoter into the host genome to cause increased expression, by removing destabilizing sequences from either the mRNA or the encoded protein by deleting that information from the host genome, or by adding stabilizing sequences to the mRNA (U.S. Pat. No. 4,910,141).

It is contemplated that more than one polynucleotide encoding a desaturase or a polynucleotide encoding more than one desaturase may be introduced and propagated in a host cell through the use of episomal or integrated expression vectors. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced polynucleotides are expressed at the necessary levels to provide for synthesis of the desired products.

When necessary for transformation, a desaturase coding sequences can be inserted into a plant transformation vector, e.g. the binary vector described by Bevan (1984). Plant transformation vectors can be derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors the tumor-inducing genes have been deleted and the functions of the vir region are utilized to transfer foreign DNA bordered by the T-DNA border sequences The T-region also contains a selectable marker for antibiotic resistance, and a multiple cloning site for inserting sequences for transfer. Such engineered strains are known as "disarmed" *A. tumefaciens* strains, and allow the efficient transformation of sequences bordered by the T-region into the nuclear genomes of plants.

The subject invention finds many applications. Probes based on the polynucleotides of the present invention may find use in methods for isolating related molecules or in methods to detect organisms expressing desaturases. When used as probes, the polynucleotides or oligonucleotides must be detectable. This is usually accomplished by attaching a label either at an internal site, for example via incorporation of a modified residue, or at the 5' or 3' terminus. Such labels can be directly detectable, can bind to a secondary molecule that is detectably labeled, or can bind to an unlabelled secondary molecule and a detectably labeled tertiary molecule; this process can be extended as long as is practical to achieve a satisfactorily detectable signal without unacceptable levels of background signal. Secondary, tertiary, or bridging systems can include use of antibodies directed against any other molecule, including labels or other antibodies, or can involve any molecules which bind to each other, for example a biotinstreptavidin/avidin system. Detectable labels typically include radioactive isotopes, molecules which chemically or enzymatically produce or alter light, enzymes which produce detectable reaction products, magnetic molecules, fluorescent molecules or molecules whose fluorescence or light-emitting characteristics change upon binding. Examples of labeling methods can be found in U.S. Pat. No. 5,011,770. Alternatively, the binding of target molecules can be directly detected by measuring the change in heat of solution on binding of probe to target via isothermal titration calorimetry, or by coating the probe or target on a surface and detecting the change in scattering of light from the surface produced by binding of target or probe, respectively, as may be done with the BIAcore system.

Constructs comprising the gene of interest may be introduced into a host cell by standard techniques. For convenience, a host cell which has been manipulated by any method to take up a DNA sequence or construct will be referred to as "transformed" or "recombinant" herein. The subject host will have at least have one copy of the expression construct and may have two or more, for example, depending upon whether the gene is integrated into the genome, amplified, or is present on an extrachromosomal element having multiple copy numbers.

The transformed host cell can be identified by selection for a marker contained on the introduced construct. Alternatively, a separate marker construct may be introduced with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene therefor may confer antibiotic resistance, or encode an essential growth factor or enzyme, and permit growth on selective media when expressed in the transformed host. Selection of a transformed host can also occur when the expressed marker protein can be detected, either directly or indirectly. The marker protein may be expressed alone or as a fusion to another protein. The marker protein can be detected by its enzymatic activity; for example, beta-galactosidase can convert the substrate X-gal to a colored product, and luciferase can convert luciferin to a light-emitting product. The marker protein can be detected by its light-producing or modifying characteristics; for example, the green fluorescent protein of *Aequorea victoria* fluoresces when illuminated with blue light. Antibodies can be used to detect the marker protein or a molecular tag on, for example a protein of interest. Cells expressing the marker protein or tag can be selected, for example, visually, or by techniques such as FACS or panning using antibodies. Desirably, resistance to kanamycin and the amino glycoside G418 are of interest, as well as ability to grow on media lacking uracil, leucine, lysine or tryptophan.

Another aspect of the present invention provides transgenic plants or progeny of plants containing the isolated DNA described herein. Plant cells may be transformed with one or more isolated DNA(s) encoding $\Delta 6$- and $\Delta 15$-desaturase by any plant transformation method. The transformed plant cell, often in a callus culture or leaf disk, is regenerated into a complete transgenic plant by methods well-known to one of ordinary skill in the art (e.g. Horsch et al., 1985). Since progeny of transformed plants inherit the polynucleotide(s) encoding the desaturase, seeds or cuttings from transformed plants may be used to maintain the transgenic plant line.

The present invention further provides a method for providing transgenic plants with an increased content of GLA and/or SDA. In certain embodiments of the invention, a DNA encoding a $\Delta 15$- and/or $\Delta 12$-desaturase may be introduced into plant cells with a $\Delta 6$ desaturase. Such plants may or may not also comprise endogenous $\Delta 12$- and/or $\Delta 15$-desaturase activity.

The present invention further provides a method for providing transgenic corn plants containing elevated levels of PUFAs including GLA and/or SDA, which are lacking in native corn plants. Expression vectors comprising DNA encoding a $\Delta 6$-desaturase, and/or a $\Delta 12$-desaturase and/or a $\Delta 15$-desaturase, can be constructed by methods of recombinant technology known to one of ordinary skill in the art (Sambrook et al., 2001).

For dietary supplementation, the purified PUFAs, transformed plants or plant parts, or derivatives thereof, may be incorporated into cooking oils, fats or margarines formulated so that in normal use the recipient would receive the desired amount. The PUFAs may also be incorporated into infant formulas, nutritional supplements or other food products, and may find use as anti-inflammatory or cholesterol lowering agents.

As used herein, "edible composition" is defined as compositions which may be ingested by a mammal such as foodstuffs, nutritional substances and pharmaceutical compositions. As used herein "foodstuffs" refer to substances that can be used or prepared for use as food for a mammal and include substances that may be used in the preparation of food (such as frying oils) or food additives. For example, foodstuffs include animals used for human consumption or any product therefrom, such as, for example, eggs. Typical foodstuffs include but are not limited to beverages, (e.g., soft drinks, carbonated beverages, ready to mix beverages), infused foods (e.g. fruits and vegetables), sauces, condiments, salad dressings, fruit juices, syrups, desserts (e.g., puddings, gelatin, icings and fillings, baked goods and frozen desserts such as ice creams and sherbets), soft frozen products (e.g., soft frozen creams, soft frozen ice creams and yoghurts, soft frozen toppings such as dairy or non-dairy whipped toppings), oils and emulsified products (e.g., shortening, margarine, mayonnaise, butter, cooking oil, and salad dressings) and intermediate moisture foods (e.g., rice and dog foods).

One example of a foodstuff provided by the invention is a food formulated for a companion animal. The term "companion animal" refers to a domesticated animal. The companion animal may be a mammal in particular, and specifically includes, but is not limited to, dogs, cats, rabbits, rodents, and horses. As described, the companion animal may obtain health benefits by consuming such a foodstuff comprising seed oil according to the invention.

The formulation of animal food products is well known to those of skill in the art, including food formulated for companion animals. In the area of cat and dog food, for example, wet pet food, semi-moist pet food, dry pet food and pet treats and snacks are well known. Drinks for pets are also available such as milk drinks for cats. An intermediate moisture food, for example, generally has a moisture content above 20% while a wet food has a moisture of at least about 65%. Semi-moist food typically has a moisture content between about 20 to about 65% and can include humectants such as propylene glycol, potassium sorbate, and other ingredients to prevent microbial (i.e., bacteria and mold) growth. Dry pet food (kibble) generally has a moisture content below about 20%, and its production may include extruding, drying and/or baking in heat. Pet treats and snacks are often semi-moist chewable treats or snacks; dry treats or snacks in any number of shapes or forms; chewable bones; baked, extruded or stamped treats; confection treats/snacks; or other kinds of treats, as is well known in the art.

An intermediate moisture pet food product may include ingredients such as cereal grains, meats, fats, vitamins, minerals, water and functional ingredients that are blended together, cooked and packaged. However, any semi-moist pet food formulation known to one skilled in the art can be used. For example, a pet food can be formed by adding, on a dry matter basis, about 5-40% by weight of protein; about 5-45% by weight of fat; about 0.1-12% by weight of a fiber; about 1-90% by weight carbohydrate, and about 0.1-2% by weight of a functional ingredient. An oil composition of the invention may added in any desired amount, for example, in about 1-50% by weight, including about 1-30% and about 3-15%. Variations may be made based on the desired characteristics of the end product, as is well known to those of skill in the art.

Furthermore, edible compositions described herein can also be ingested as an additive or supplement contained in foods and drinks. These can be formulated together with a nutritional substance such as various vitamins and minerals and incorporated into substantially liquid compositions such as nutrient drinks, soymilks and soups; substantially solid compositions; and gelatins or used in the form of a powder to be incorporated into various foods. The content of the effective ingredient in such a functional or health food can be similar to the dose contained in a typical pharmaceutical agent.

The purified PUFAs, transformed plants or plant parts may also be incorporated into animal, particularly livestock, feed. In this way, the animals themselves may benefit from a PUFA rich diet, while human consumers of food products produced from such livestock may benefit as well. It is expected in certain embodiments that SDA will be converted to EPA in animals and thus such animals may benefit from an increase in EPA by consumption of SDA.

For pharmaceutical use (human or veterinary), the compositions may generally be administered orally but can be administered by any route by which they may be successfully absorbed, e.g., parenterally (i.e. subcutaneously, intramuscularly or intravenously), rectally, vaginally or topically, for example, as a skin ointment or lotion. The PUFAs, transformed plants or plant parts of the present invention may be administered alone or in combination with a pharmaceutically acceptable carrier or excipient. Where available, gelatin capsules are the preferred form of oral administration. Dietary supplementation as set forth above can also provide an oral route of administration. The unsaturated acids of the present invention may be administered in conjugated forms, or as salts, esters, amides or prodrugs of the fatty acids. Any pharmaceutically acceptable salt is encompassed by the present invention; especially preferred are the sodium, potassium or lithium salts. Also encompassed are the N-alkylpolyhydroxamine salts, such as N-methyl glucamine, found in PCT publication WO 96/33155. The preferred esters are the ethyl esters. As solid salts, the PUFAs also can be administered in tablet form. For intravenous administration, the PUFAs or derivatives thereof may be incorporated into commercial formulations such as Intralipids.

In certain embodiments of the invention, coding sequences or fragments thereof are provided operably linked to a heterologous promoter, in either sense or antisense orientation. Expression constructs are also provided comprising these sequences, as are plants and plant cells transformed with the sequences. The construction of constructs which may be employed in conjunction with plant transformation techniques using these or other sequences according to the invention will be known to those of skill of the art in light of the present disclosure (see, for example, Sambrook et al., 2001; Gelvin et al., 1990). The techniques of the current invention are thus not limited to any particular nucleic acid sequences.

One use of the sequences provided by the invention will be in the alteration of oil composition. The desaturase gene may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

The choice of any additional elements used in conjunction with the desaturase coding sequences will often depend on the purpose of the transformation. One of the major purposes of transformation of crop plants is to add commercially desirable, agronomically important traits to the plant. As PUFAs are known to confer many beneficial effects on health, concomitant increases in SDA production may also be beneficial and could be achieved by expression of Primula Δ6-desaturase. Such increasing of SDA may, in certain embodiments of the invention, comprise expression of Δ12 and/or Δ15 desaturase.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce various desaturase encoding nucleic acids. Introduction of such sequences may be facilitated by use of bacterial or yeast artificial chromosomes (BACs or YACs, respectively), or even plant artificial chromosomes. For example, the use of BACs for Agrobacterium-mediated transformation was disclosed by Hamilton et al. (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait, and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

Transformation constructs prepared in accordance with the invention will typically include a 3' end DNA sequence that acts as a signal to terminate transcription and allow for the poly-adenylation of the mRNA produced by coding sequences operably linked to a desaturase gene (e.g., cDNA). In one embodiment of the invention, the native terminator of a desaturase gene is used. Alternatively, a heterologous 3' end may enhance the expression of desaturase coding regions. Examples of terminators deemed to be useful include those from the nopaline synthase gene of *Agrobacterium tumefaciens* (nos 3' end) (Bevan et al., 1983), the 3' end of the protease inhibitor I or II genes from potato or tomato and the CaMV 35S terminator. Regulatory elements such as an Adh intron (Callis et al., 1987), sucrose synthase intron (Vasil et al., 1989) or TMV omega element (Gallie et al., 1989), may further be included where desired.

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention, as is well known in the art. In this case, one would then generally assay the potentially transformed cell population by exposing the cells to a selective agent or agents, or one would screen the cells for the desired marker gene trait.

In addition to direct transformation of a particular plant genotype with a construct prepared according to the current invention, transgenic plants may be made by crossing a plant having a selected DNA of the invention to a second plant lacking the DNA. Plant breeding techniques may also be used to introduce a multiple desaturases, for example Δ6, Δ12, and/or Δ15-desaturase(s) into a single plant. In this manner, the product of a Δ6-desaturase reaction can be effectively increased. By creating plants homozygous for a Δ6-desaturase gene and/or other desaturase genes (e.g., Δ12- and/or Δ15-desaturase genes) beneficial metabolites can be increased in the plant.

As set forth above, a selected desaturase gene can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes or alleles relative to a starting plant line, as disclosed herein, is defined as the techniques that result in a particular sequence being introduced into a plant line by crossing a starting line with a donor plant line that comprises a transgene or allele of the invention. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

Backcrossing is herein defined as the process including the steps of: (a) crossing a plant of a first genotype containing a desired gene, DNA sequence or element to a plant of a second genotype lacking said desired gene, DNA sequence or element; (b) selecting one or more progeny plant containing the desired gene, DNA sequence or element; (c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Vectors for Expression of Δ15- and Δ6-Desaturases in Corn

A binary vector was constructed to express a Δ15-desaturase and a Δ6-desaturase in corn embryo and aleurone tissue. This construct was prepared with the globulin promoter driving expression of a *Neurospora crassa* Δ15-desaturase mutagenized to increase expression in a monocot such as corn (SEQ ID NO:5) and of a *Mortierella alpina* Δ6 desaturase (SEQ ID NO:6, bp 71-1444) (U.S. Pat. No. 6,075,183). The *M. alpina* Δ6 desaturase was cloned into a shuttle vector containing the globulin promoter, pMON67624, resulting in pMON82809. The mutagenized *N. crassa* Δ15 desaturase was cloned into a shuttle vector containing the globulin promoter, pMON67624, resulting in pMON82810.

The two globulin desaturase expression cassettes were then cloned into the pMON30167 corn binary vector containing the CP4 marker gene for glyphosate resistance. The first expression cassette containing the *M. alpina* Δ6 desaturase was cloned into pMON30167, resulting in pMON82811. The second expression cassette containing the mutagenized *N. crassa* Δ15 desaturase was then cloned into pMON82811, resulting in corn transformation construct pMON82812 (FIG. 1). Transformed explants are obtained via *Agrobacterium tumefaciens*-mediated transformation. Plants are regenerated from transformed tissue. The greenhouse-grown plants are then analyzed for oil composition.

Figure 2:
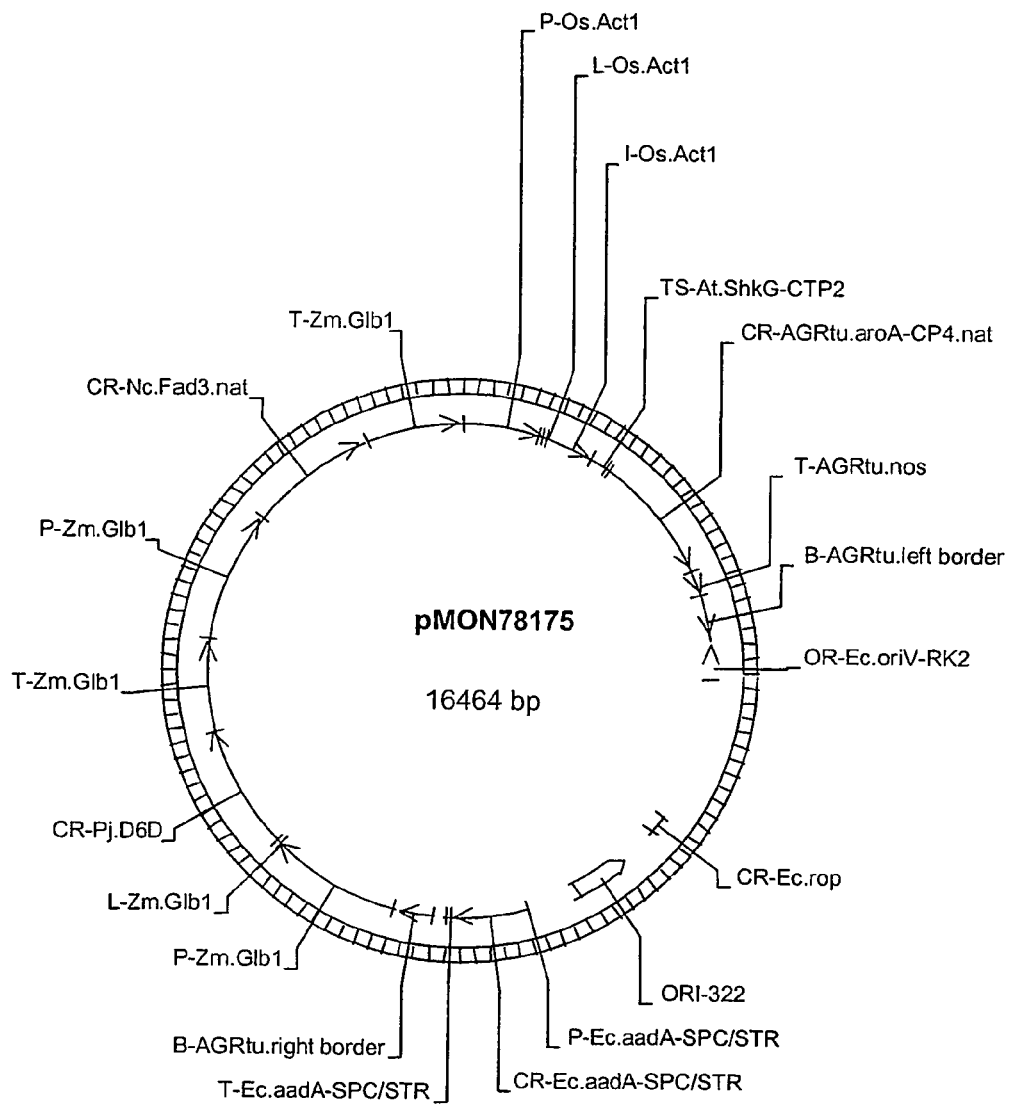
FIG. 2 shows a map of vector pMON78175.

Another binary vector, pMON78175 was constructed to express a Δ15-desaturase and a Δ6-desaturase in corn embryo and aleurone tissue. To generate the binary vector, an expression cassette containing the *N. crassa* Δ15 desaturase (SEQ ID NO:5) under the control of the globulin promoter was PCR-amplified using pMONS2812 as a template, cloned into a shuttle vector, and the cassette sequence-verified. The expression cassette containing the *P. juliae* Δ6-desaturase (SEQ ID NO: 7) driven by the globulin promoter was generated by PCR. As part of this process, the nucleotides immediately preceding the ATG-start codon of the *P. juliae* Δ6-desaturase were changed to CAGCC, to generate a translation initiation region optimized for gene expression in monocotyledonous plants such as corn. Using standard restriction and ligation procedures that are well established in the art, the *P. juliae* Δ6-desaturase and the *N. crassa* Δ15 desaturase were subsequently cloned into a binary vector harboring a CP4 expression cassette as selectable marker to generate the corn transformation vector, pMON78175 (FIG. 2). Transformed explants are obtained via *Agrobacterium tumefaciens*-mediated transformation. Plants are regenerated from transformed tissue. The greenhouse-grown plants are then analyzed for oil composition.

Example 2

Vector for Expression of a Monocotyledonous Sequence-optimized *Primula Juliae* Δ6 Desaturase in Corn This example sets forth the design and construction of a *Primula juliae* Δ6 desaturase polynucleotide molecule modified for expression in monocotyledonous plants. It is well known in the art that non-endogenous protein-encoding sequences may not express well in plants (U.S. Pat. No. 5,880,275, herein incorporated by reference). Therefore, using a native PjD6D polypeptide sequence (SEQ ID NO: 3), an artificial PjD6D protein-encoding polynucleotide sequence was designed and constructed by 1) using a codon usage bias similar to that of highly expressed monocot proteins, and by 2) removal of RNA destabilizing elements previously characterized and known to affect mRNA stability in planta (U.S. Pat. No. 5,880,275). The resulting modified PjD6D polynucleotide sequence was designated PjD6Dnno (SEQ ID NO: 8) and encodes a polypeptide identical in sequence to the native PjD6D polypeptide (SEQ ID NO: 3).

Figure 3:
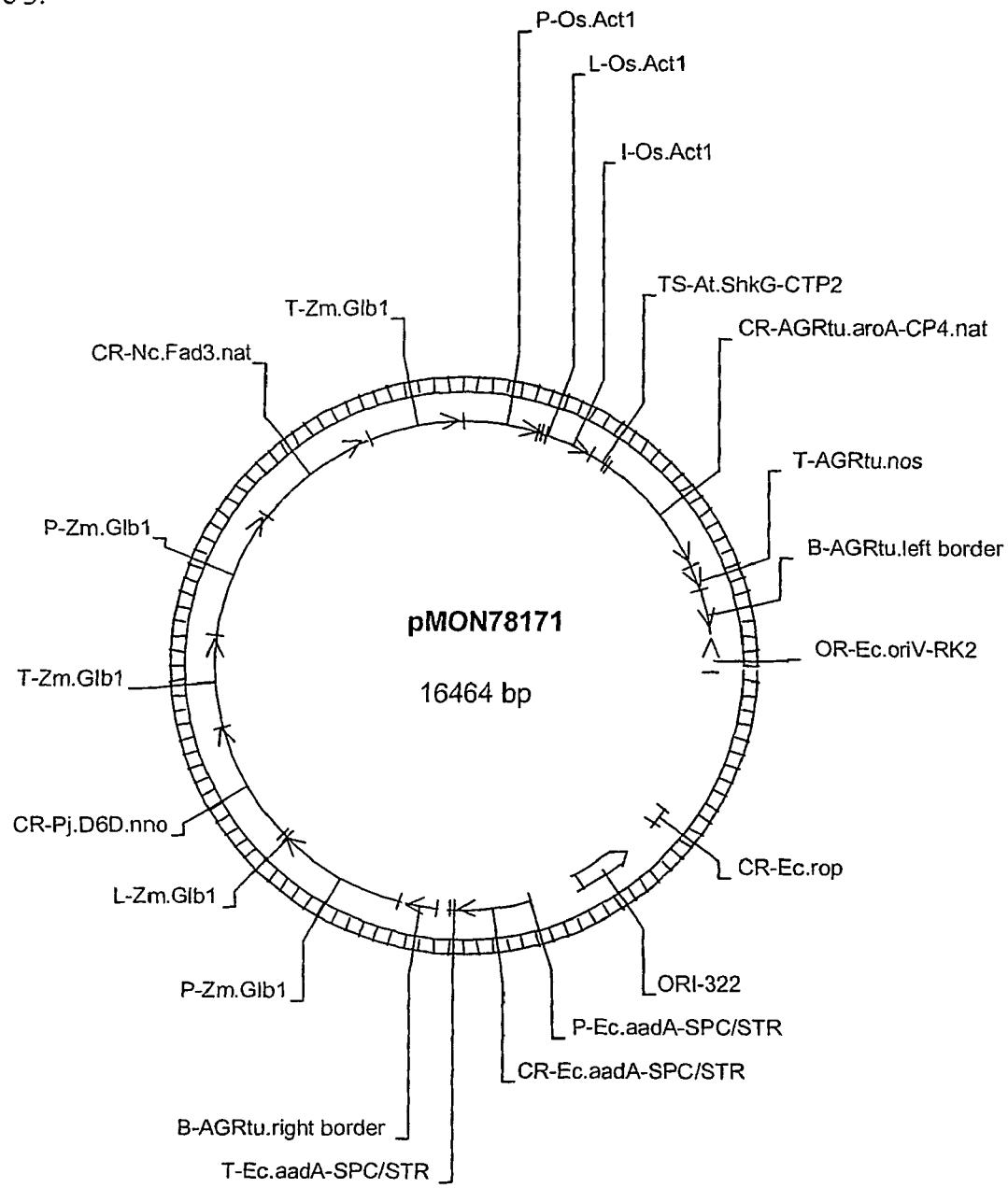
FIG. 3 shows a map of vector pMON78171.

A binary vector, pMON78171 was constructed to express a Δ15-desaturase and the sequence-modified Δ6-desaturase in corn embryo and aleurone tissue. To generate the binary vector, an expression cassette containing the *N. crassa* Δ15 desaturase (SEQ ID NO:5) under the control of the globulin promoter was PCR-amplified using pMON82812 as a template, cloned into a shuffle vector, and the cassette sequence-verified. The expression cassette containing the *P. juliae* Δ6-desaturase (SEQ ID NO:9) driven by the globulin promoter was generated by PCR. As part of this process, the nucleotides immediately preceding the ATG-start codon of the *P. juliae* Δ6-desaturase were changed to CAGCC, to generate a translation initiation region optimized for gene expression in monocotyledonous plants, such as corn. Using standard restriction and ligation procedures that are well established in the art the *P. juliae* Δ6-desaturase and the *N. crassa* Δ15 desaturase were subsequently cloned into a binary vector harboring a CP4 expression cassette as selectable marker to generate the corn transformation vector, pMON78171 (FIG. 3). Transformed explants are obtained via *Agrobacterium tumefaciens*-mediated transformation. Plants are regenerated from transformed tissue. The greenhouse-grown plants are then analyzed for oil composition.

Example 3

Fatty Acid Analysis

Fatty acid composition of mature kernels expressing pMON82812 was determined by grinding corn kernels and extracting the homogenate with heptane. The heptane extract was treated with toluene containing triheptadecanoin at 0.25 mg/ml and sodium methoxide in methanol (0.6 N). The reaction was stopped with aqueous sodium chloride (10% wt/vol). After partitioning at room temperature, the organic phase was analyzed by GLC (Hewlett Packard model 6890 (120 volt) equipped with a split/splitless capillary inlet (250° C.) and a flame ionization detector (270° C.). The column was a Supelco 24077 (0.25 mm od.×15 m length) with a 0.25 µm bonded polyethylene glycol stationary phase. The fatty acid methyl esters are identified by retention time comparison to commercial standards. Qualitative weight percent compositions are calculated as area percents of identified peaks. The results of the analysis for kernels that exhibited SDA and GLA are given in Table 1. Partial null kernels containing only GLA were not found. Overall, more than two thirds of the kernels analyzed contained GLA and SDA. The analysis of a mature kernel from event ZM_103111:@, which was transformed with pMON82812, demonstrated 9.68% SDA.

TABLE 1

Fatty Acid Analysis of Single Mature Corn Kernels Expressing SDA and/or GLA

| Pedigree | Gen | Oleic (18:1) | LA (18:2) | GLA (18:3) | ALA (18:3) | SDA (18:4) |
|---|---|---|---|---|---|---|
| ZM_S103111:@. | R1 | 26.08 | 13.62 | 0.91 | 26.44 | 9.68 |
| ZM_S103432:@. | R1 | 23.63 | 14.87 | 0.85 | 30.17 | 8.56 |

TABLE 1-continued

Fatty Acid Analysis of Single Mature Corn Kernels Expressing SDA and/or GLA

| Pedigree | Gen | Oleic (18:1) | LA (18:2) | GLA (18:3) | ALA (18:3) | SDA (18:4) |
|---|---|---|---|---|---|---|
| ZM_S103121:@. | R1 | 27.39 | 16.2 | 1.14 | 27.61 | 5.8 |
| ZM_S103432:@. | R1 | 21.44 | 14.11 | 0.68 | 36.19 | 5.79 |
| ZM_S103111:@. | R1 | 25.5 | 16.36 | 0.61 | 30.56 | 5.19 |
| ZM_S103435/LH244 | F1 | 22.3 | 16.98 | 0.99 | 33.28 | 4.81 |
| ZM_S103435/LH244 | F1 | 23.85 | 19.52 | 0.84 | 29.91 | 4.21 |
| ZM_S103121:@. | R1 | 26.2 | 15.07 | 1.11 | 32.29 | 3.93 |
| ZM_S103432:@. | R1 | 20.38 | 18.37 | 0.85 | 35.49 | 3.84 |
| ZM_S103121:@. | R1 | 25.07 | 17.73 | 0.77 | 30.96 | 3.78 |
| ZM_S103110:@. | R1 | 21.57 | 18.99 | 0.68 | 34.07 | 3.69 |
| ZM_S103432:@. | R1 | 19.99 | 19.61 | 0.78 | 34.71 | 3.69 |
| ZM_S103110:@. | R1 | 22.17 | 18.57 | 0.58 | 34.81 | 3.67 |
| ZM_S103427:@. | R1 | 18.42 | 23.76 | 1.01 | 32.27 | 3.61 |
| ZM_S103435/LH244 | F1 | 20.83 | 19.3 | 0.68 | 34.71 | 3.53 |
| ZM_S103427:@. | R1 | 19.17 | 25.22 | 1.53 | 30.79 | 3.53 |
| ZM_S103110:@. | R1 | 22.12 | 17.73 | 0.79 | 34.38 | 3.48 |
| ZM_S103099/LH244 | F1 | 20.26 | 21.88 | 0.75 | 32.13 | 3.4 |
| ZM_S103432:@. | R1 | 16.98 | 18.61 | 0.8 | 40.32 | 3.27 |
| ZM_S103432:@. | R1 | 21.18 | 19.65 | 0.73 | 34.34 | 3.25 |
| ZM_S103111:@. | R1 | 24.59 | 19.08 | 0.35 | 30.79 | 3.23 |
| ZM_S103111:@. | R1 | 21.29 | 19.93 | 0.71 | 33.77 | 3.23 |
| ZM_S103099/LH244 | F1 | 21.11 | 23.29 | 0.79 | 30.95 | 3.21 |
| ZM_S103432:@. | R1 | 18.2 | 18.81 | 0.61 | 38.94 | 3.19 |
| ZM_S103435/LH244 | F1 | 21.27 | 19.75 | 0.7 | 34.33 | 3.13 |
| ZM_S103432:@. | R1 | 20.8 | 21.47 | 0.76 | 33.59 | 3.12 |
| ZM_S103121:@. | R1 | 23.71 | 18.96 | 0.75 | 31.97 | 3.1 |
| ZM_S103121:@. | R1 | 23.81 | 17.28 | 0.98 | 33.75 | 3.07 |
| ZM_S103099/LH244 | F1 | 19.64 | 21.46 | 0.7 | 34.49 | 2.99 |
| ZM_S103121:@. | R1 | 23.83 | 16.72 | 1.01 | 34.5 | 2.93 |
| ZM_S103427:@. | R1 | 16.68 | 26.92 | 1.03 | 30.59 | 2.87 |
| ZM_S103168/LH244 | F1 | 18.58 | 23.81 | 1.34 | 32.42 | 2.87 |
| ZM_S103432:@. | R1 | 17.94 | 18.89 | 0.72 | 39.8 | 2.84 |
| ZM_S103110:@. | R1 | 20.14 | 19.32 | 0.58 | 36.65 | 2.77 |
| ZM_S103111:@. | R1 | 20.57 | 19.13 | 0.34 | 36.1 | 2.7 |
| ZM_S103168/LH244 | F1 | 20.04 | 25.44 | 1.26 | 30.32 | 2.69 |
| ZM_S103110:@. | R1 | 21.6 | 19.78 | 0.61 | 35.15 | 2.66 |
| ZM_S103099/LH244 | F1 | 21.06 | 23.54 | 0.67 | 31.49 | 2.58 |
| ZM_S103435/LH244 | F1 | 19.26 | 22.53 | 0.9 | 34.92 | 2.53 |
| ZM_S103433/LH244 | F1 | 22.95 | 20.01 | 0.39 | 33.51 | 2.47 |
| ZM_S103168/LH244 | F1 | 19.39 | 26.31 | 1.23 | 31.06 | 2.4 |
| ZM_S103110:@. | R1 | 18.05 | 22.96 | 0.65 | 35.53 | 2.39 |
| ZM_S103110:@. | R1 | 18.99 | 21.92 | 0.65 | 35.22 | 2.38 |
| ZM_S103111:@. | R1 | 17.14 | 22.59 | 0.71 | 36.95 | 2.32 |
| ZM_S103433/LH244 | F1 | 23.64 | 19.84 | 0.38 | 33.12 | 2.29 |
| ZM_S103436/LH244 | F1 | 20.71 | 26.64 | 1.07 | 28.11 | 2.26 |
| ZM_S103435/LH244 | F1 | 21.89 | 21.12 | 0.6 | 33.35 | 2.24 |
| ZM_S103110:@. | R1 | 22.59 | 28.35 | 0.52 | 25.05 | 2.15 |
| ZM_S103168/LH244 | F1 | 19.41 | 27.76 | 1.19 | 28.96 | 2.14 |
| ZM_S103168/LH244 | F1 | 17.81 | 28.33 | 1.28 | 31.34 | 2.1 |
| ZM_S103097/LH244 | F1 | 18.61 | 25.34 | 1.19 | 31.88 | 2.09 |
| ZM_S103168/LH244 | F1 | 20.08 | 28.05 | 1.27 | 28.28 | 2.06 |
| ZM_S103433/LH244 | F1 | 20.11 | 19.18 | 0.38 | 38.29 | 2.04 |
| ZM_S103427:@. | R1 | 18.38 | 30.32 | 1.19 | 26.79 | 1.98 |
| ZM_S103427:@. | R1 | 20.06 | 29.56 | 1.13 | 27.23 | 1.95 |
| ZM_S103436/LH244 | F1 | 19.82 | 28.13 | 0.89 | 28.57 | 1.94 |
| ZM_S103110:@. | R1 | 18.74 | 22.83 | 0.72 | 35.29 | 1.91 |
| ZM_S103433/LH244 | F1 | 21.69 | 21.09 | 0.4 | 34.71 | 1.9 |
| ZM_S103430/LH244 | F1 | 23.25 | 25.64 | 0.92 | 27.64 | 1.89 |
| ZM_S103099/LH244 | F1 | 17.77 | 25.43 | 0.61 | 33.61 | 1.88 |
| ZM_S103111:@. | R1 | 21.04 | 22.99 | 0.29 | 31.6 | 1.86 |
| ZM_S103168/LH244 | F1 | 18.19 | 27.7 | 1.18 | 31.55 | 1.86 |
| ZM_S103099/LH244 | F1 | 18.24 | 23.16 | 0.65 | 35.78 | 1.85 |
| ZM_S103435/LH244 | F1 | 21.02 | 27.67 | 0.88 | 28.27 | 1.83 |
| ZM_S103433/LH244 | F1 | 21.7 | 21.08 | 0.39 | 34.49 | 1.8 |
| ZM_S103097/LH244 | F1 | 20.11 | 26.32 | 1.08 | 29.94 | 1.8 |
| ZM_S103427:@. | R1 | 16.95 | 30.23 | 1.08 | 30.11 | 1.8 |
| ZM_S103437/LH244 | F1 | 23.93 | 26.23 | 1.12 | 25.86 | 1.78 |
| ZM_S103437/LH244 | F1 | 23.5 | 26.49 | 0.99 | 26.32 | 1.77 |
| ZM_S103168/LH244 | F1 | 19.4 | 27.81 | 1.06 | 30.29 | 1.74 |
| ZM_S103427:@. | R1 | 17.94 | 30.11 | 1.17 | 29.42 | 1.74 |
| ZM_S103103/LH244 | F1 | 21.32 | 31.31 | 1.16 | 24.36 | 1.66 |
| ZM_S103433/LH244 | F1 | 20.48 | 21.06 | 0.41 | 35.4 | 1.64 |
| ZM_S103437/LH244 | F1 | 19.71 | 26.4 | 1.06 | 31.7 | 1.6 |
| ZM_S103433/LH244 | F1 | 18.98 | 21.89 | 0.36 | 37.18 | 1.59 |
| ZM_S103430/LH244 | F1 | 21.41 | 26.76 | 0.91 | 27.06 | 1.56 |
| ZM_S103437/LH244 | F1 | 18.67 | 28.15 | 1.07 | 30.71 | 1.56 |

TABLE 1-continued

Fatty Acid Analysis of Single Mature Corn Kernels Expressing SDA and/or GLA

| Pedigree | Gen | Oleic (18:1) | LA (18:2) | GLA (18:3) | ALA (18:3) | SDA (18:4) |
|---|---|---|---|---|---|---|
| ZM_S103097/LH244 | F1 | 19.97 | 28.13 | 1.18 | 28.16 | 1.55 |
| ZM_S103436/LH244 | F1 | 19.29 | 31.27 | 0.79 | 25.74 | 1.53 |
| ZM_S103430/LH244 | F1 | 22.43 | 25.58 | 0.81 | 28.41 | 1.53 |
| ZM_S103430/LH244 | F1 | 18.48 | 27.25 | 1.05 | 31.73 | 1.53 |
| ZM_S103103/LH244 | F1 | 21.25 | 31.91 | 1.13 | 24.06 | 1.53 |
| ZM_S103435/LH244 | F1 | 20.92 | 27.87 | 0.82 | 27.48 | 1.51 |
| ZM_S103121:@. | R1 | 20 | 24.11 | 0.99 | 33.48 | 1.5 |
| ZM_S103103/LH244 | F1 | 20.9 | 31.44 | 1.08 | 25.09 | 1.5 |
| ZM_S103103/LH244 | F1 | 20.06 | 32.22 | 1.04 | 25.4 | 1.4 |
| ZM_S103103/LH244 | F1 | 20.02 | 33.05 | 1.09 | 24.5 | 1.39 |
| ZM_S103097/LH244 | F1 | 18.78 | 28.78 | 1.03 | 29.82 | 1.31 |
| ZM_S103111:@. | R1 | 19.23 | 27.51 | 0.62 | 29.58 | 1.25 |
| ZM_S103436/LH244 | F1 | 18.53 | 30.87 | 0.66 | 27.55 | 1.22 |
| LH244/ZM_S103431 | F1 | 20.88 | 23.22 | 0.34 | 32.46 | 1.19 |
| LH244/ZM_S103431 | F1 | 20.07 | 25.05 | 0.35 | 33.01 | 1.19 |
| ZM_S103436/LH244 | F1 | 20.39 | 31.62 | 0.69 | 26.02 | 1.16 |
| ZM_S103111:@. | R1 | 20.48 | 24.18 | 0.47 | 32.33 | 1.11 |
| ZM_S103435/LH244 | F1 | 20.4 | 26.7 | 0.52 | 31.26 | 1.09 |
| ZM_S103436/LH244 | F1 | 19.35 | 31.69 | 0.71 | 27.3 | 1.08 |
| LH244/ZM_S103431 | F1 | 19.75 | 23.35 | 0.26 | 33.86 | 0.98 |
| ZM_S103436/LH244 | F1 | 20.11 | 32.54 | 0.71 | 26.25 | 0.96 |
| ZM_S103430/LH244 | F1 | 18.87 | 29.25 | 0.7 | 30.17 | 0.95 |
| LH244/ZM_S103431 | F1 | 21.18 | 25.86 | 0.2 | 29.33 | 0.87 |
| LH244/ZM_S103098 | F1 | 21.77 | 24.64 | 0.15 | 32.57 | 0.81 |
| LH244/ZM_S103105 | F1 | 17.72 | 32.84 | 0.41 | 27.61 | 0.68 |
| ZM_S103434/LH244 | F1 | 20.34 | 26.19 | 0.3 | 31.48 | 0.6 |
| ZM_S103434/LH244 | F1 | 21.59 | 26.44 | 0.28 | 29.99 | 0.58 |
| ZM_S103434/LH244 | F1 | 20.22 | 27.13 | 0.31 | 30.47 | 0.58 |
| LH244/ZM_S103098 | F1 | 19.29 | 27.08 | 0.19 | 33.6 | 0.52 |
| ZM_S103434/LH244 | F1 | 19.24 | 28.24 | 0.26 | 31.45 | 0.51 |
| LH244/ZM_S103105 | F1 | 17.73 | 34.46 | 0.44 | 27.24 | 0.5 |
| LH244/ZM_S103431 | F1 | 19.12 | 31.08 | 0.24 | 27.77 | 0.47 |
| ZM_S103434/LH244 | F1 | 17.63 | 29.39 | 0.24 | 32.47 | 0.38 |
| LH244/ZM_S103105 | F1 | 18.37 | 36.34 | 0.36 | 24.68 | 0.33 |
| LH244/ZM_S103105 | F1 | 18.62 | 38.05 | 0.34 | 22.84 | 0.27 |
| ZM_S103110:@. | R1 | 18.35 | 57.16 | 0 | 2.25 | 0 |
| LH244/ZM_S103098 | F1 | 19.18 | 58.95 | 0 | 1.78 | 0 |
| LH244/ZM_S103098 | F1 | 19.35 | 58.56 | 0 | 1.79 | 0 |
| LH244/ZM_S103098 | F1 | 19.17 | 59.15 | 0 | 1.8 | 0 |
| LH244/ZM_S103098 | F1 | 16.76 | 62.23 | 0 | 1.81 | 0 |
| LH244/ZM_S103098 | F1 | 18.39 | 59.37 | 0 | 1.88 | 0 |
| LH244/ZM_S103098 | F1 | 18.26 | 59.91 | 0 | 1.96 | 0 |
| LH244/ZM_S103098 | F1 | 17.14 | 61.34 | 0 | 2.06 | 0 |
| LH244/ZM_S103098 | F1 | 16.65 | 61.17 | 0 | 2.39 | 0 |

Fatty acid analysis of events generated by transformation with pMON78171 are shown in Table 2 below. Ten mature R1 or F1 seed were analyzed for their fatty acid composition as above, and average fatty acid composition was calculated from those numbers, excluding the nulls. The best performing event obtained with vector pMON78171 contained on average 28.6% SDA, and 2.2% GLA. The best performing single corn seed contained 32.9% SDA and 3.5% GLA.

TABLE 2

Fatty Acid Analysis of Mature Corn Kernels

| Pedigree | Gen | Oleic | LA | GLA | ALA | SDA |
|---|---|---|---|---|---|---|
| ZM_S126797:@. | R1 | 21.34 | 12.92 | 3.53 | 13.49 | 32.92 |
| ZM_S126797:@. | R1 | 22.11 | 12.12 | 3.3 | 14.12 | 32.58 |
| ZM_S126797:@. | R1 | 21.91 | 12.87 | 3.5 | 13.1 | 32.28 |
| ZM_S127034:@. | R1 | 23.26 | 9.86 | 1.22 | 17.05 | 31.2 |
| ZM_S126797:@. | R1 | 24.07 | 14.98 | 3.24 | 13.06 | 28.74 |
| ZM_S128026/LH244 | F1 | 21.96 | 16.99 | 3.24 | 12.69 | 28.5 |
| ZM_S127034:@. | R1 | 24.15 | 11.3 | 1.2 | 18.06 | 28.19 |
| ZM_S129919:@. | R1 | 21.79 | 17.34 | 2.43 | 14.1 | 28.19 |
| ZM_S127034:@. | R1 | 27.39 | 9.56 | 1.28 | 16.03 | 28.04 |
| ZM_S127034:@. | R1 | 29.01 | 9.8 | 1.19 | 15.19 | 27.41 |
| ZM_S128026/LH244 | F1 | 22.35 | 17.95 | 3.58 | 12.5 | 26.93 |
| ZM_S129919:@. | R1 | 20.77 | 19.48 | 3.02 | 14.79 | 26.51 |
| ZM_S127034:@. | R1 | 25.09 | 12.21 | 1.29 | 17.85 | 26.4 |
| ZM_S127034:@. | R1 | 22.99 | 15.22 | 1.3 | 18.47 | 25.87 |
| ZM_S127034:@. | R1 | 21.95 | 19.77 | 4.66 | 11.88 | 25.81 |
| ZM_S127034:@. | R1 | 26.95 | 13.34 | 1.35 | 15.95 | 25.62 |
| ZM_S126797:@. | R1 | 20.94 | 20.76 | 4.4 | 13.5 | 24.7 |
| ZM_S126790/LH244 | F1 | 24.46 | 19.05 | 2.71 | 13.05 | 24.57 |
| ZM_S128026/LH244 | F1 | 23.44 | 19.46 | 3.71 | 12.28 | 24.24 |
| ZM_S126797:@. | R1 | 21.41 | 22.02 | 4.87 | 11.41 | 23.95 |
| ZM_S126808:@. | R1 | 25.61 | 18.44 | 2.38 | 14.16 | 23.81 |
| ZM_S126797:@. | R1 | 22.74 | 20.52 | 4.23 | 12.86 | 23.8 |
| ZM_S126797:@. | R1 | 20.95 | 22.77 | 4.76 | 11.94 | 23.74 |
| ZM_S126808:@. | R1 | 22 | 19.57 | 2.76 | 16.21 | 23.64 |
| ZM_S129919:@. | R1 | 21.49 | 23.45 | 2.95 | 13.33 | 22.4 |
| ZM_S128026/LH244 | F1 | 23.12 | 22.18 | 3.87 | 12.33 | 22.34 |
| ZM_S126797:@. | R1 | 21.51 | 24.35 | 4.56 | 12 | 21.82 |
| ZM_S126790/LH244 | F1 | 25.99 | 20.48 | 2.46 | 13.48 | 21.71 |
| ZM_S126995/LH244 | F1 | 24.4 | 22.45 | 2.12 | 14.26 | 20.03 |
| ZM_S126790/LH244 | F1 | 24.33 | 23.6 | 2.87 | 13.24 | 19.76 |
| ZM_S126790/LH244 | F1 | 24.24 | 24.08 | 2.88 | 12.74 | 19.44 |

TABLE 2-continued

Fatty Acid Analysis of Mature Corn Kernels

| Pedigree | Gen | Oleic | LA | GLA | ALA | SDA |
|---|---|---|---|---|---|---|
| ZM_S126995/LH244 | F1 | 29.51 | 20.1 | 1.96 | 12.44 | 19.17 |
| ZM_S126800/LH244 | F1 | 26.18 | 24.62 | 3.01 | 11.52 | 18.9 |
| ZM_S126800/LH244 | F1 | 24.35 | 26.28 | 3.26 | 10.89 | 18.56 |
| ZM_S129919:@. | R1 | 21.87 | 27.84 | 2.77 | 12.76 | 18.28 |
| ZM_S126995/LH244 | F1 | 26.78 | 24.15 | 2.09 | 11.97 | 18.26 |
| ZM_S129919:@. | R1 | 21.22 | 28.87 | 3 | 12.33 | 18.18 |
| ZM_S126800/LH244 | F1 | 23.23 | 27.22 | 3.54 | 11.35 | 17.98 |
| ZM_S126790/LH244 | F1 | 22.01 | 28.63 | 3.36 | 12.63 | 17.78 |
| ZM_S126995/LH244 | F1 | 26.48 | 23.9 | 1.84 | 12.93 | 17.78 |
| ZM_S126800/LH244 | F1 | 26.6 | 25.01 | 2.72 | 11.7 | 17.54 |
| ZM_S126995/LH244 | F1 | 25.83 | 25.52 | 2.12 | 12.59 | 17.15 |
| ZM_S129919:@. | R1 | 21.8 | 30 | 2.79 | 11.51 | 16.89 |
| ZM_S129919:@. | R1 | 20.77 | 31.81 | 3.03 | 11.33 | 16.65 |
| ZM_S126808:@. | R1 | 22.22 | 30.61 | 2.64 | 11.91 | 16.07 |
| ZM_S126808:@. | R1 | 22.6 | 30.58 | 2.5 | 11.72 | 15.54 |
| ZM_S126800/LH244 | F1 | 23.86 | 31.07 | 3.13 | 11.37 | 15.07 |
| ZM_S126800/LH244 | F1 | 26.73 | 29.67 | 2.92 | 9.6 | 14.26 |
| ZM_S126995/LH244 | F1 | 31.78 | 22.68 | 1.87 | 12.32 | 14.07 |
| ZM_S126808:@. | R1 | 22.94 | 33.24 | 2.81 | 10.51 | 13.79 |
| ZM_S126808:@. | R1 | 21.28 | 34.77 | 3.15 | 10.62 | 13.65 |
| ZM_S126808:@. | R1 | 25.73 | 32.94 | 2.19 | 9.26 | 11.95 |
| ZM_S128026/LH244 | F1 | 18.81 | 62.08 | 0.09 | 1.61 | 0.7 |
| ZM_S126790/LH244 | F1 | 19.23 | 62.98 | 0 | 1.36 | 0.06 |
| ZM_S126790/LH244 | F1 | 19.62 | 63.27 | 0 | 1.18 | 0 |
| ZM_S126790/LH244 | F1 | 19.56 | 63.19 | 0 | 1.38 | 0 |
| ZM_S126790/LH244 | F1 | 19.88 | 61.96 | 0 | 1.3 | 0 |
| ZM_S126790/LH244 | F1 | 20.43 | 61.28 | 0 | 1.37 | 0 |
| ZM_S126800/LH244 | F1 | 22.09 | 59.61 | 0 | 1.22 | 0 |
| ZM_S126800/LH244 | F1 | 20.09 | 62.11 | 0 | 1.32 | 0 |
| ZM_S126800/LH244 | F1 | 21.8 | 59.52 | 0 | 1.34 | 0 |
| ZM_S126800/LH244 | F1 | 22.55 | 59.63 | 0 | 1.28 | 0 |
| ZM_S126808:@. | R1 | 20.9 | 60.65 | 0 | 1.43 | 0 |
| ZM_S126808:@. | R1 | 20.57 | 60.95 | 0 | 1.54 | 0 |
| ZM_S126808:@. | R1 | 18.75 | 62.61 | 0 | 1.45 | 0 |
| ZM_S126995/LH244 | F1 | 20.03 | 63.35 | 0 | 1.22 | 0 |
| ZM_S126995/LH244 | F1 | 21.55 | 59.59 | 0 | 1.1 | 0 |
| ZM_S126995/LH244 | F1 | 24.63 | 56.02 | 0 | 1.12 | 0 |
| ZM_S126995/LH244 | F1 | 20.12 | 60.75 | 0 | 1.23 | 0 |
| ZM_S126998:@. | R1 | 21.51 | 60 | 0 | 1.62 | 0 |
| ZM_S126998:@. | R1 | 22.17 | 27.15 | 0 | 34.29 | 0 |
| ZM_S126998:@. | R1 | 19.77 | 62.76 | 0 | 1.61 | 0 |
| ZM_S126998:@. | R1 | 20.73 | 28.41 | 0 | 33.75 | 0 |
| ZM_S126998:@. | R1 | 20.59 | 33.96 | 0 | 29.47 | 0 |
| ZM_S126998:@. | R1 | 20.8 | 33.48 | 0 | 28.9 | 0 |
| ZM_S126998:@. | R1 | 22.15 | 33.67 | 0 | 27.92 | 0 |
| ZM_S126998:@. | R1 | 19.86 | 30.92 | 0 | 32.91 | 0 |
| ZM_S126998:@. | R1 | 21.47 | 30.99 | 0 | 31.39 | 0 |
| ZM_S126998:@. | R1 | 21.37 | 31.16 | 0 | 30.85 | 0 |
| ZM_S127034:@. | R1 | 19.76 | 62.38 | 0 | 1.36 | 0 |
| ZM_S127034:@. | R1 | 19.99 | 62.51 | 0 | 1.26 | 0 |
| ZM_S127034:@. | R1 | 20.76 | 61.27 | 0 | 1.25 | 0 |
| ZM_S128026/LH244 | F1 | 20.86 | 59.51 | 0 | 1.63 | 0 |
| ZM_S128026/LH244 | F1 | 18.57 | 63.07 | 0 | 1.38 | 0 |
| ZM_S128026/LH244 | F1 | 19.7 | 62.41 | 0 | 1.13 | 0 |
| ZM_S128026/LH244 | F1 | 19.8 | 61.53 | 0 | 1.2 | 0 |
| ZM_S128026/LH244 | F1 | 17.96 | 65.06 | 0 | 1.32 | 0 |
| ZM_S129919:@. | R1 | 20.7 | 60.71 | 0 | 1.29 | 0 |
| ZM_S129919:@. | R1 | 20.04 | 61.49 | 0 | 1.45 | 0 |
| ZM_S129919:@. | R1 | 19.53 | 61.77 | 0 | 1.37 | 0 |

Fatty acid analysis of events generated by transformation with pMON78175 are shown in Table 3 below. Ten mature R1 or F1 seed were analyzed for their fatty acid composition as above. The best performing single corn seed contained 12.4% SDA and 0% GLA.

TABLE 3

Fatty Acid Analysis of Mature Corn Kernels

| Pedigree | Gen | Oleic acid | Linoleic acid | GLA | ALA | SDA |
|---|---|---|---|---|---|---|
| ZM_S130139:@. | R1 | 26.57 | 8.39 | 0 | 34.39 | 12.36 |
| ZM_S130134:@. | R1 | 30.59 | 9.04 | 0 | 30.31 | 11.86 |
| ZM_S130135:@. | R1 | 26.39 | 9.41 | 0 | 34.91 | 11.12 |
| ZM_S130135:@. | R1 | 25.09 | 12.98 | 0.12 | 34.81 | 9.93 |
| ZM_S130133:@. | R1 | 30.62 | 10.85 | 0 | 30.93 | 9.63 |
| ZM_S130136:@. | R1 | 30.55 | 11.99 | 0 | 32.28 | 7.63 |
| ZM_S130136:@. | R1 | 28.27 | 13.53 | 0 | 33.41 | 7.45 |
| ZM_S130136:@. | R1 | 29.14 | 10.61 | 0 | 34.59 | 7.44 |
| ZM_S130134:@. | R1 | 25.43 | 14.32 | 0 | 35.68 | 7.3 |
| ZM_S130134:@. | R1 | 23.94 | 16.92 | 0 | 35.7 | 6 |
| ZM_S130133:@. | R1 | 22.93 | 17.14 | 0.02 | 37.21 | 5.88 |
| ZM_S130136:@. | R1 | 28.28 | 11.89 | 0 | 35.63 | 5.86 |
| ZM_S130140:@. | R1 | 23.47 | 15.34 | 0 | 37.85 | 5.68 |
| ZM_S130133:@. | R1 | 21.75 | 17.83 | 0 | 37.43 | 5.59 |
| ZM_S130072/LH244 | F1 | 23.17 | 25.78 | 0.2 | 28.61 | 5.39 |
| ZM_S130140:@. | R1 | 22.75 | 17.26 | 0 | 37.98 | 4.83 |
| ZM_S130161:@. | R1 | 28.54 | 13.26 | 0 | 37.6 | 2.88 |
| ZM_S130140:@. | R1 | 20.82 | 23.51 | 0 | 35.48 | 2.88 |
| ZM_S130155/LH244 | F1 | 20.87 | 59.43 | 0 | 2.2 | 0 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,826,877
U.S. Pat. No. 4,910,141
U.S. Pat. No. 5,011,770
U.S. Pat. No. 5,158,975
U.S. Pat. No. 5,302,523
U.S. Pat. No. 5,378,619
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,591,616
U.S. Pat. No. 5,952,544
U.S. Pat. No. 6,603,061
Ausubel et al., In: Current Protocols in Molecular Biology, Green Publishing Assoc., NY, 1994.
Baerson et al., *Plant Mol. Biol.*, 22(2):255-267, 1993.
Bevan et al., *Nucleic Acids Res.*, 11(2):369-385, 1983.
Bevan, *Nucleic Acids Res.*, 12:8111, 1984.
Bustos et al., *J. Bacteriol.*, 174:7525-7533, 1991.
Bustos, et al., *Plant Cell*, 1(9):839-853, 1989.

Callis et al., *Genes Dev.*, 1:1183-1200, 1987.
Chen et al., *Proc. Natl. Acad. Sci. USA*, 83:8560-8564, 1986.
Chou and Fasman, *Adv. Enzymol.*, 47:45-148, 1978.
de Deckerer, *Eur. J. Clin. Nutr.*, 52:749, 1998.
Garcia-Maroto et al., *Lipids*, 37 (4), 2002
Gelvin et al., In: *Plant Molecular Biology Manual*, 1990.
Goeddel, In: *Methods in Enzymology*, Perbal (Ed.), Academic Press, John Wiley and Sones, 185, 1988.
Hamilton et al., Proc. Natl. Acad. Sci. USA, 93(18):9975-9979, 1996.
Hong et al., Plant Mol. Biol., 34(3):549-555, 1997.
Horrobin et al., *Am. J. Clin. Nutr.*, 57(Suppl):732S-737S, 1993.
Horsch et al., *Science*, 227:1229, 1985.
Huang, *Biochem. Biophys. Acta*, 1082:319, 1991.
James et al., *Semin. Arthritis Rheum.*, 28:85, 2000.
Kaeppler et al., *Plant Cell Reports*, 9:415-418, 1990.
Koncz and Schell, *Mol. Gen. Genet.*, 204:383-396, 1986.
Kridl et al., *Seed Sci. Res.*, 1:209:219, 1991.
Kyte and Doolittle, *J. Mol. Biol.*, 157:105-132, 1982.
Manzioris et al., *Am. J. Clin. Nutr.*, 59:1304, 1994.
Michaelis et al., *Ann. Rev. Microbiol.*, 36:425, 1982.
Napier et al., Biochem J. 328, 717-720, 1997.
Napier et al., *Prostaglandins Leukot. Essent. Fatty Acids*, 68 (2), 135-143, 2003.
Naylor et al., *Nature*, 405:1017, 2000.
Omirulleh et al., *Plant Mol. Biol.*, 21(3):415-28, 1993.
PCT Appl. US03/16144
PCT Appl. WO 96/33155
PCT Appl. WO 03/06870
Pedersen et al., *Cell*, 29:1015-1026, 1982.
Potrykus et al., *Mol. Gen. Genet.*, 199(2):169-77, 1985.
Potrykus et al., *Mol. Gen. Genet.*, 199:183-188, 1985.
Radke et al., *Plant Cell Reports*, 11:499-505, 1992.
Reed et al., *Plant Physiol.*, 122:715-720, 2000.
Riggs, et al., *Plant Cell*, 1(6):609-621, 1989.
Russell et al., *Transgenic Res.*, 6(2):157-168
Sambrook et al., In: *Molecular cloning*, Cold Spring Harbor Laboratory Press, Cold Spring Harbor, N.Y., 2001.
Sayanova et al., *FEBS Let.*, 542:100-104, 2003.
Sayanova et al., *Plant Physiol.*, 121, 641-646, 1999.
Shanklin et al., *Biochemisty* 33, 12787-12794, 1994.
Simopoulos et al., *Am. Coll. Nutri.*, 18:487, 1999.
Slocombe et al., *Plant Physjsiol.*, 104(4):167-176, 1994.
Sperling and Heinz, *Eur. J. Lipid Sci. Technolo.*, 103, 158-180, 2001.
Van den Broeck et al., *Nature*, 313:358, 1985.
Vasil et al., Plant Physiol., 91:1575-1579, 1989.
Yang et al. *Proc. Natl. Acad. Sci. USA*, 87:4144-4148, 1990.
Wolk et al., *Proc. Natl. Acad. Sci. USA*, 1561-1565, 1984.
Yamazaki et al., *Biochem. Biophys. Acta*, 1123:18, 19992.

The invention claimed is:

1. A corn seed comprising an endogenous corn seed oil having a stearidonic acid (18:4 n-3) content of from about 5% to about 33%, wherein the ratio of stearidonic acid to gamma-linolenic acid is about 3:1 or higher.

2. The corn seed of claim 1, defined as an inbred seed.

3. The corn seed of claim 1, defined as a hybrid seed.

4. A corn plant that produces an endogenous corn seed oil having a stearidonic acid (18:4 n-3) content of from about 5% to about 33%, wherein the ratio of stearidonic acid to gamma-linolenic acid is at least about 3:1.

5. The corn plant of claim 4, defined as an inbred plant.

6. The corn plant of claim 4, defined as a hybrid plant.

7. A method of producing seed oil, comprising growing the plant of claim 4 under plant growth conditions until the plant produces said seed oil.

* * * * *

UNITED STATES PATENT AND TRADEMARK OFFICE
CERTIFICATE OF CORRECTION

| | | |
|---|---|---|
| PATENT NO. | : 8,378,186 B2 | Page 1 of 1 |
| APPLICATION NO. | : 11/578447 | |
| DATED | : February 19, 2013 | |
| INVENTOR(S) | : Ursin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1249 days.

Signed and Sealed this
Thirtieth Day of December, 2014

Michelle K. Lee
*Deputy Director of the United States Patent and Trademark Office*

SEQUENCE LISTING

```
<160> NUMBER OF SEQ ID NOS: 22

<210> SEQ ID NO 1
<211> LENGTH: 1953
<212> TYPE: DNA
<213> ORGANISM: Primula juliae

<400> SEQUENCE: 1
tatatatata tatatatata atcccaaaca aacactgtca cttgcaaaac aaactcaacc      60
cacgttactt atcccttttc cccaaaatgg aaaacacatt ttcaccacca cctactaaca     120
ccaattccaa ccccatgact aagaccattt acataaccag ctcagaactt gaaaaacata     180
acaagccagg tgacctatgg atatcaattc acggtcaagt ttacgacgtt tcttcctggg     240
ctgcgcttca cccgggggc atcgctcccc tcctcgccct tgcaggacat gatgtgaccg      300
acgctttcct cgcttaccat cccccctycca cctcccgcct cctccctccc ttctccacca    360
acctacttct agaaaaacat tccgtgtccg agacctcttc cgactatcgc aaacttctag     420
acagctttca taagatgggc atgtttcgtg ccaggggcca cactgcctac gcgaccttg      480 tcattatgat acttatgttg gtttcctctg tgactgggt gctttgcagt gagaatccgt      540
gggtgcattt ggtttgtgga gcggcaatgg ggtttgcctg gatccagtgc ggatggatag     600
gtcatgattc cggacattac cggataatga ctgacaggaa atggaaccgg ttcgctcaga     660
tcctgagctc aaactgcctc caagggatta gtatcgggtg gtggaagtgg aaccacaacg     720
cgcaccacat tgcctgcaat agtctggagt acgaccctga cctccagtac attcccttgt     780
tggttgtgtc cccgaagttc tttaactccc tcacttctcg tttctacgac aagaagctga     840
acttcgacgg tgtgtcgagg ttttttggttc aataccagca ctggtcgttt tatccggtca    900
tgtgtgttgc taggctgaac atgcttgcgc agtcgtttat actgcttttt tcgaggaggg     960
aggtggcgaa cagggtgcag gagattcttg gactagcggt tttttggctt tggtttccgc    1020
tcctgctttc ttgccttcct aattggggtg agagaataat gttttttgctc gcgagctact   1080
```

```
ccgttacggg gatacaacac gtgcagttca gcttgaacca tttctcatct gacgtttacg   1140
tgggcccacc cgtaggtaac gattggttta agaaacagac tgcagggaca ctcaacatat   1200
cgtgcccggc gtggatggat tggttccacg gtggattgca gtttcaggtc gagcaccact   1260
tgttcccgcg gatgcctagg ggtcagtttc ggaagatttc tcctttttgtg agggatttgt   1320
gtaagaaaca caatttgact tacaatattg cgtcttttac taaagcaaat gtgttgacgc   1380
ttgagaccct gagaaacaca gccattgagg ctcgggacct ctctaatccg atcccaaaga   1440
atatggtgtg ggaggctgtt aaaaatgtcg ggtgaaattg actatgtgtt ttgctattgg   1500
agcttcaatt tcgtgattgt cgtttaaggg ggtatacaca atcaccagat aatcaaacgt   1560
tttctgttgt atttcgttct tgttatttac atttgtagag tggctcatgt aactgacttg   1620
tgtcgaatcg ttaagcctaa atacaagtgt aacaatttag tttctgtcca atttgagaaa   1680
tagaaaagtt tggttgagcc ttttttttct tctaatttct tcaacaggct tattgagtgc   1740
cttatttgcc acatacttaa gcgaaatgct ccaagtgcgc tagccgcaga tgtataaatt   1800
gtcttttcg gcttcaagtt ttaactgtat aacgtcattt cggcttatcg taatggttca   1860
aattagctgc ttttgttttg acaattgtcc taagcaggca ctgatcaaca ctatcagttg   1920
ttctttccct ggtaaaaaag aactgttgaa ttt                                1953

<210> SEQ ID NO 2
<211> LENGTH: 1341
<212> TYPE: DNA
<213> ORGANISM: Primula juliae

<400> SEQUENCE: 2
atgactaaga ccatttacat aaccagctca gaacttgaaa aacataacaa gccaggtgac     60
ctatggatat caattcacgg tcaagtttac gacgtttctt cctgggctgc gcttcacccg    120
gggggcatcg ctcccctcct cgccttgca ggacatgatg tgaccgacgc tttcctcgct    180
taccatcccc cttccaccct ccgcctcctc cctcccttct ccaccaacct acttctagaa    240
aaacattccg tgtccgagac ctcttccggc tatcgcaaac ttctagacag cttttcataag   300
atgggcatgt tcgtgccag gggccacact gcctacgcga ccttgtcat tatgatactt     360
atgttggttt cctctgtgac tggggtgctt tgcagtgaga atccgtgggt gcatttggtt    420
tgtggagcgg caatggggtt tgcctggatc cagtgcggat ggataggtca tgattccgga    480
cattaccgga taatgactga caggaaatgg aaccggttcg ctcagatcct gagctcaaac    540
tgcctccaag ggattagcat cgggtggtgg aagtggaacc acaacgcgca ccacattgcc    600
tgcaatagtc tggagtacga ccctgacctc cagtacattc ccttgttggt tgtgtccccg    660
aagttcttta actccctcac ttctcgtttc tacgacaaga agctgaactt cgacggtgtg    720
tcgaggtttt tggttcaata ccagcactgg tcgttttatc cggtcatgtg tgttgctagg    780
ctgaacatgc ttgcgcagtc gtttatactg cttttttcga ggagggaggt ggcgaacagg    840
gtgcaggaga ttcttggact agcgttttt tggctttggt ttccgctcct gctttcttgc    900
cttcctaatt ggggtgagag aataatgttt ttgctcgcga gctactccgt tacggggata    960
caacacgtgc agttcagctt gaaccatttc tcatctgacg tttacgtggg cccacccgta   1020
ggtaacgatt ggtttaagaa acagactgca gggacactca acatatcgtg cccggcgtgg   1080
atggattggt ccatggcgg gttgcagttt caggtcgagc accacttgtt cccgcggatg   1140
cctaggggtc agtttcggaa gatttctcct tttgtgaggg atttgtgtaa gaaacacaat   1200
ttgacttaca atattgcgtc tttactaaa gcaaatgtgt tgacgcttga gaccctgaga   1260
```

```
aacacagcca ttgaggctcg ggacctctct aatccgatcc caaagaatat ggtgtgggag   1320
gctgttaaaa atgtcgggtg a                                             1341
```

<210> SEQ ID NO 3
<211> LENGTH: 1389
<212> TYPE: DNA
<213> ORGANISM: Primula juliae

<400> SEQUENCE: 3

```
atggaaaaca cattttcacc accacctact aacaccaatt ccaacccat gactaagacc     60 atttacataa ccagctcaga acttgaaaaa cataacaagc caggtgacct atggatatca   120
attcacggtc aagtttacga cgtttcttcc tgggctgcgc ttcacccggg gggcatcgct   180
cccctcctcg cccttgcagg acatgatgtg accgacgctt cctcgctta ccatccccct    240 tccacctccc gcctcctccc tcccttctcc accaacctac ttctagaaaa acattccgtg   300
tccgagacct cttccgacta cgcaaactt ctagacagct tcataagat gggcatgttt     360 cgtgccagag ccacactgc ctacgcgacc tttgtcatta tgatacttat gttggtttcc    420
tctgtgactg gggtgctttg cagtgagaat ccgtgggtgc atttggtttg tggagcggca   480
atggggtttg cctggatcca gtgcggatgg ataggtcatg attccggaca ttaccggata   540
atgactgaca ggaaatggaa ccggttcgct cagatcctga gctcaaactg cctccaaggg   600
attagcatcg ggtggtggaa gtggaaccac aacgcgcacc acattgcctg caatagtctg   660
gagtacgacc ctgacctcca gtacattccc ttgttggttg tgtccccgaa gttctttaac   720
tccctcactt ctcgtttcta cgacaagaag ctgaacttcg acggtgtgtc gaggtttttg   780
gttcaatacc agcactggtc gttttatccg gtcatgtgtg ttgctaggct gaacatgctt   840
gcgcagtcgt ttatactgct tttttcgagg agggaggtgg cgaacagggt gcaggagatt   900
cttggactag cggttttttg gctttggttt ccgctcctgc tttcttgcct tcctaattgg   960
ggtgagagaa taatgttttt gctcgcgagc tactccgtta cggggataca acacgtgcag  1020
ttcagcttga accatttctc atctgacgtt acgtgggcc cacccgtagg taacgattgg   1080
tttaagaaac agactgcagg gacactcaac atatcgtgcc cggcgtggat ggattggttc  1140
catggcgggt tgcagtttca ggtcgagcac cacttgttcc cgcggatgcc tagggggtcag 1200 tttcggaaga tttctccttt tgtgagggat tgtgtaaga aacacaatttt gacttacaat   1260 attgcgtctt ttactaaagc aaatgtgttt acgcttgaga ccctgagaaa cacagccatt  1320
gaggctcggg acctctctaa tccgatccca aagaatatgg tgtgggaggc tgttaaaaat  1380
gtcgggtga                                                          1389
```

<210> SEQ ID NO 4
<211> LENGTH: 446
<212> TYPE: PRT
<213> ORGANISM: Primula juliae

<400> SEQUENCE: 4

```
Met Thr Lys Thr Ile Tyr Ile Thr Ser Ser Glu Leu Glu Lys His Asn
1               5                   10                  15

Lys Pro Gly Asp Leu Trp Ile Ser Ile His Gly Gln Val Tyr Asp Val
            20                  25                  30

Ser Ser Trp Ala Ala Leu His Pro Gly Gly Ile Ala Pro Leu Leu Ala
        35                  40                  45

Leu Ala Gly His Asp Val Thr Asp Ala Phe Leu Ala Tyr His Pro Pro
    50                  55                  60
```

| | | | | | | | | | | | | | | | |
|---|---|---|---|---|---|---|---|---|---|---|---|---|---|---|---|
Ser Thr Ser Arg Leu Leu Pro Pro Phe Ser Thr Asn Leu Leu Leu Glu
 65                  70                  75                  80

Lys His Ser Val Ser Glu Thr Ser Ser Asp Tyr Arg Lys Leu Leu Asp
                 85                  90                  95

Ser Phe His Lys Met Gly Met Phe Arg Ala Arg Gly His Thr Ala Tyr
            100                 105                 110

Ala Thr Phe Val Ile Met Ile Leu Met Leu Val Ser Ser Val Thr Gly
        115                 120                 125

Val Leu Cys Ser Glu Asn Pro Trp Val His Leu Val Cys Gly Ala Ala
    130                 135                 140

Met Gly Phe Ala Trp Ile Gln Cys Gly Trp Ile Gly His Asp Ser Gly
145                 150                 155                 160

His Tyr Arg Ile Met Thr Asp Arg Lys Trp Asn Arg Phe Ala Gln Ile
                165                 170                 175

Leu Ser Ser Asn Cys Leu Gln Gly Ile Ser Ile Gly Trp Trp Lys Trp
            180                 185                 190

Asn His Asn Ala His His Ile Ala Cys Asn Ser Leu Glu Tyr Asp Pro
        195                 200                 205

Asp Leu Gln Tyr Ile Pro Leu Leu Val Val Ser Pro Lys Phe Phe Asn
    210                 215                 220

Ser Leu Thr Ser Arg Phe Tyr Asp Lys Lys Leu Asn Phe Asp Gly Val
225                 230                 235                 240

Ser Arg Phe Leu Val Gln Tyr Gln His Trp Ser Phe Tyr Pro Val Met
                245                 250                 255

Cys Val Ala Arg Leu Asn Met Leu Ala Gln Ser Phe Ile Leu Leu Phe
            260                 265                 270

Ser Arg Arg Glu Val Ala Asn Arg Val Gln Ile Leu Gly Leu Ala
        275                 280                 285

Val Phe Trp Leu Trp Phe Pro Leu Leu Leu Ser Cys Leu Pro Asn Trp
290                 295                 300

Gly Glu Arg Ile Met Phe Leu Leu Ala Ser Tyr Ser Val Thr Gly Ile
305                 310                 315                 320

Gln His Val Gln Phe Ser Leu Asn His Phe Ser Ser Asp Val Tyr Val
                325                 330                 335

Gly Pro Pro Val Gly Asn Asp Trp Phe Lys Lys Gln Thr Ala Gly Thr
            340                 345                 350

Leu Asn Ile Ser Cys Pro Ala Trp Met Asp Trp Phe His Gly Gly Leu
        355                 360                 365

Gln Phe Gln Val Glu His His Leu Phe Pro Arg Met Pro Arg Gly Gln
    370                 375                 380

Phe Arg Lys Ile Ser Pro Phe Val Arg Asp Leu Cys Lys Lys His Asn
385                 390                 395                 400

Leu Thr Tyr Asn Ile Ala Ser Phe Thr Lys Ala Asn Val Leu Thr Leu
                405                 410                 415

Glu Thr Leu Arg Asn Thr Ala Ile Glu Ala Arg Asp Leu Ser Asn Pro
            420                 425                 430

Ile Pro Lys Asn Met Val Trp Glu Ala Val Lys Asn Val Gly
        435                 440                 445

<210> SEQ ID NO 5
<211> LENGTH: 462
<212> TYPE: PRT
<213> ORGANISM: Primula juliae

<400> SEQUENCE: 5

```
Met Glu Asn Thr Phe Ser Pro Pro Thr Asn Thr Asn Ser Asn Pro
1               5                   10                  15

Met Thr Lys Thr Ile Tyr Ile Thr Ser Ser Glu Leu Glu Lys His Asn
            20                  25                  30

Lys Pro Gly Asp Leu Trp Ile Ser Ile His Gly Gln Val Tyr Asp Val
            35                  40                  45

Ser Ser Trp Ala Ala Leu His Pro Gly Gly Ile Ala Pro Leu Leu Ala
50                  55                  60

Leu Ala Gly His Asp Val Thr Asp Ala Phe Leu Ala Tyr His Pro Pro
65              70                  75                  80

Ser Thr Ser Arg Leu Leu Pro Pro Phe Ser Thr Asn Leu Leu Leu Glu
                85                  90                  95

Lys His Ser Val Ser Glu Thr Ser Ser Asp Tyr Arg Lys Leu Leu Asp
            100                 105                 110

Ser Phe His Lys Met Gly Met Phe Arg Ala Arg Gly His Thr Ala Tyr
            115                 120                 125

Ala Thr Phe Val Ile Met Ile Leu Met Leu Val Ser Ser Val Thr Gly
            130                 135                 140

Val Leu Cys Ser Glu Asn Pro Trp Val His Leu Val Cys Gly Ala Ala
145                 150                 155                 160

Met Gly Phe Ala Trp Ile Gln Cys Gly Trp Ile Gly His Asp Ser Gly
                165                 170                 175

His Tyr Arg Ile Met Thr Asp Arg Lys Trp Asn Arg Phe Ala Gln Ile
                180                 185                 190

Leu Ser Ser Asn Cys Leu Gln Gly Ile Ser Ile Gly Trp Trp Lys Trp
            195                 200                 205

Asn His Asn Ala His His Ile Ala Cys Asn Ser Leu Glu Tyr Asp Pro
            210                 215                 220

Asp Leu Gln Tyr Ile Pro Leu Leu Val Val Ser Pro Lys Phe Phe Asn
225                 230                 235                 240

Ser Leu Thr Ser Arg Phe Tyr Asp Lys Lys Leu Asn Phe Asp Gly Val
                245                 250                 255

Ser Arg Phe Leu Val Gln Tyr Gln His Trp Ser Phe Tyr Pro Val Met
                260                 265                 270

Cys Val Ala Arg Leu Asn Met Leu Ala Gln Ser Phe Ile Leu Leu Phe
            275                 280                 285

Ser Arg Arg Glu Val Ala Asn Arg Val Gln Glu Ile Leu Gly Leu Ala
            290                 295                 300

Val Phe Trp Leu Trp Phe Pro Leu Leu Leu Ser Cys Leu Pro Asn Trp
305                 310                 315                 320

Gly Glu Arg Ile Met Phe Leu Leu Ala Ser Tyr Ser Val Thr Gly Ile
                325                 330                 335

Gln His Val Gln Phe Ser Leu Asn His Phe Ser Ser Asp Val Tyr Val
            340                 345                 350

Gly Pro Pro Val Gly Asn Asp Trp Phe Lys Lys Gln Thr Ala Gly Thr
            355                 360                 365

Leu Asn Ile Ser Cys Pro Ala Trp Met Asp Trp Phe His Gly Gly Leu
            370                 375                 380

Gln Phe Gln Val Glu His His Leu Phe Pro Arg Met Pro Arg Gly Gln
385                 390                 395                 400

Phe Arg Lys Ile Ser Pro Phe Val Arg Asp Leu Cys Lys Lys His Asn
                405                 410                 415

Leu Thr Tyr Asn Ile Ala Ser Phe Thr Lys Ala Asn Val Leu Thr Leu
```

```
              420                 425                 430
Glu Thr Leu Arg Asn Thr Ala Ile Glu Ala Arg Asp Leu Ser Asn Pro
        435                 440                 445

Ile Pro Lys Asn Met Val Trp Glu Ala Val Lys Asn Val Gly
    450                 455                 460

<210> SEQ ID NO 6
<211> LENGTH: 24
<212> TYPE: DNA
<213> ORGANISM: Artificial
<220> FEATURE:
<223> OTHER INFORMATION: Primer

<400> SEQUENCE: 6
atmagyatyg gttggtggaa rtgg                                          24

<210> SEQ ID NO 7
<211> LENGTH: 23
<212> TYPE: DNA
<213> ORGANISM: Artificial
<220> FEATURE:
<223> OTHER INFORMATION: Primer

<400> SEQUENCE: 7
aatccaccrt graaccartc cat                                           23

<210> SEQ ID NO 8
<211> LENGTH: 27
<212> TYPE: DNA
<213> ORGANISM: Artificial
<220> FEATURE:
<223> OTHER INFORMATION: Primer

<400> SEQUENCE: 8
cacacatgac cggataaaac gaccagt                                       27

<210> SEQ ID NO 9
<211> LENGTH: 27
<212> TYPE: DNA
<213> ORGANISM: Artificial
<220> FEATURE:
<223> OTHER INFORMATION: Primer

<400> SEQUENCE: 9
gggaatgtac tggaggtcag ggtcgta                                       27

<210> SEQ ID NO 10
<211> LENGTH: 27
<212> TYPE: DNA
<213> ORGANISM: Artificial
<220> FEATURE:
<223> OTHER INFORMATION: Primer

<400> SEQUENCE: 10
cgtgcagttc agcttgaacc atttctc                                       27

<210> SEQ ID NO 11
<211> LENGTH: 27
<212> TYPE: DNA
<213> ORGANISM: Artificial
<220> FEATURE:
<223> OTHER INFORMATION: Primer

<400> SEQUENCE: 11
tgcagggaca ctcaacatat cgtgccc                                       27
```

```
<210> SEQ ID NO 12
<211> LENGTH: 27
<212> TYPE: DNA
<213> ORGANISM: Artificial
<220> FEATURE:
<223> OTHER INFORMATION: Primer

<400> SEQUENCE: 12
gtaggttggt ggagaaggga gggagga                                          27

<210> SEQ ID NO 13
<211> LENGTH: 27
<212> TYPE: DNA
<213> ORGANISM: Artificial
<220> FEATURE:
<223> OTHER INFORMATION: Primer

<400> SEQUENCE: 13
ggaaggggga tggtaagcga ggaaagc                                          27

<210> SEQ ID NO 14
<211> LENGTH: 33
<212> TYPE: DNA
<213> ORGANISM: Artificial
<220> FEATURE:
<223> OTHER INFORMATION: Primer

<400> SEQUENCE: 14
gtcgacatgg aaaacacatt ttcaccacca cct                                   33

<210> SEQ ID NO 15
<211> LENGTH: 33
<212> TYPE: DNA
<213> ORGANISM: Artificial
<220> FEATURE:
<223> OTHER INFORMATION: Primer

<400> SEQUENCE: 15
gtcgacatga ctaagaccat ttacataacc agc                                   33

<210> SEQ ID NO 16
<211> LENGTH: 34
<212> TYPE: DNA
<213> ORGANISM: Artificial
<220> FEATURE:
<223> OTHER INFORMATION: Primer

<400> SEQUENCE: 16
cctgcaggtc acccgacatt tttaacagcc tccc                                  34

<210> SEQ ID NO 17
<211> LENGTH: 1290
<212> TYPE: DNA
<213> ORGANISM: Neurospora crassa

<400> SEQUENCE: 17
atggctgtca ctactaggtc acacaaagcc gccgctgcca ccgaacctga agttgtgtct      60
acaggagtgg atgcagtcag cgctgccgca ccaagcagta gtagctcctc atcctcccaa     120
aagtcagctg agcctatcga atatccagac atcaagacaa ttcgtgacgc tataccagac     180
cactgcttta gacctcgcgt ttggatatcc atggcgtact ttattcgcga ttttgcaatg     240
gctttcggcc tcggatactt ggcatggcaa tacatccctt tgattgcaag taccccattg     300
agatacggag cttgggcttt gtacggttac ctccagggac tcgtctgtac tggaatttgg     360
```

-continued

| | |
|---|---|
| atcttggctc acgaatgcgg tcacggagcc tttctagac acacctggtt caacaacgtt | 420 |
| atgggttgga ttggtcactc tttcctacta gtcccatatt ttagctggaa attttcccat | 480 |
| caccgtcatc ataggttcac cggacatatg gaaaagata tggcgttcgt tccagccacg | 540 |
| gaggcggaca gaaatcagag aaaactagct aatctctata tggacaaaga gactgcggag | 600 |
| atgttcgagg atgttcctat tgtgcagttg gttaaactaa ttgctcacca actcgccggt | 660 |
| tggcagatgt atctcttgtt caacgttagt gccggaaaag ctccaaaca gtgggaaacc | 720 |
| ggcaaaggtg gaatgggatg gctccgcgtg agccatttcg aaccaagttc agccgttttc | 780 |
| agaaacagcg aagcaattta catagctcta agcgatctcg gacttatgat tatgggatac | 840 |
| attctctacc aggcagccca agttgttgga tggcaaatgg ttggtctctt gtattttcaa | 900 |
| cagtacttct gggttcacca ttggctcgtt gccatcactt accttcatca cacacacgaa | 960 |
| gaagttcacc actttgatgc agattcttgg acatttgtta agggtgccct cgctaccgtg | 1020 |
| gacagagact tcggtttcat cggcaagcac ctcttccata acatcattga ccatcatgtt | 1080 |
| gttcatcacc tcttcccaag aatcccttc tactacgctg aagaagctac caattcaata | 1140 |
| agacctatgc tcggacctct ttaccacaga gatgaccgtt ctttcatggg gcaactctgg | 1200 |
| tacaacttca cacactgcaa atgggttgtc cctgatcctc aagtgccagg tgctctaatc | 1260 |
| tgggctcaca ccgttcagag tactcagtaa | 1290 |

<210> SEQ ID NO 18
<211> LENGTH: 1209
<212> TYPE: DNA
<213> ORGANISM: Aspergillus nidulans

<400> SEQUENCE: 18

| | |
|---|---|
| atggccgcaa ccgcgaccac tctcgctgaa atagaaaaga agaaggaaga gattacacta | 60 |
| cagacaatca agaatgccat accaaagcac tgttttaacc gtagtttgct tatttcaagt | 120 |
| gcctacgtcg tcagagacct cctctacgca tcagttttgt tctatttgc acttcatatt | 180 |
| gatacgctct tctcatccca gctccttagg atcttggcat ggacagctta cggtttcatg | 240 |
| caaggctgcg tgggaacggg tatatggata ttggcacatg aatgcggaca cggagctttt | 300 |
| agcccttacc aaacctggaa cgacgttgtt gggtggaccc ttcattctct tctcatggtc | 360 |
| ccttacttct cttggaaaat aacccacgca aggcaccaca gatatacgaa caataccgag | 420 |
| agggacacag ccttcgttcc ctggaccgag aaggaatacg acaccagacc tcgttacttc | 480 |
| cctgcatggt tcgagatgtt tgaagacaca ccagtgtata acttgatttc attgctcgcc | 540 |
| catcagatcg ccggctggca aatgtacctc tgcttctacg tctcagccgg agccaaaagt | 600 |
| aagcctgttc cacaaggcaa gcagtccgga tggtttggag gtcaacaatc tgcatcacac | 660 |
| tttgacccag gaagctctct atggaccgaa aaccagcgcc atctaatcgc aatctccgac | 720 |
| cttggactcc ttctcgtggc cgccgcgaat tggtacttgg ctcaacaagt tggtgttcta | 780 |
| agaatggtgc tcatttacgt cgtcccctac ttttgggtcc accactggct agtcgccatc | 840 |
| acgtacctcc accacactca cccatcccata ccacactaca ccgactctac ctggacattc | 900 |
| actaaaggag cactctcaac agtggatcgt gacttcggat ttataggaag gcacttcttt | 960 |
| caccacatca ttgatcacca cgtcgttcat cacttgttca ataggatacc attctatcac | 1020 |
| gcagaggaag ctactaacgc aataataccca gttctcggtg atatgtacca tagagaagaa | 1080 |
| accggattcc tctggagtct tatggaaact tataaaaact gtcgctttgt tggcgtggag | 1140 |
| aacgatgtgg gtaaggaggg agttctccat tgggttttcg aagaaaagaa aggcgctaaa | 1200 | gctgaatag                                                                    1209

<210> SEQ ID NO 19
<211> LENGTH: 1290
<212> TYPE: DNA
<213> ORGANISM: Neurospora crassa

<400> SEQUENCE: 19
atgacggtca ccacccgcag ccacaaggcc gcggccgcca ccgagcccga ggttgtcagc      60
accggcgttg acgccgtctc tgctgctgct ccctcctcct cctcctcctc ttccagccaa     120
aagtcggccg agcccatcga ataccccgac atcaagacca tccgcgacgc catccccgac     180
cactgcttcc gcccgcgcgt ctggatctcc atggcctact tcatccgcga cttcgccatg     240
gcctttggcc tcggctacct cgcctggcag tacatccccc tgatcgcctc caccccgctc     300
cgctacggcg cctgggctct gtacggctac ctccagggtc tcgtctgcac gggcatctgg     360
attctggcgc acgagtgcgg ccacggcgcc ttctcgaggc acacgtggtt caacaacgtc     420
atggggtgga ttggccactc cttcctcttg gtcccttact tcagctggaa gttcagccac     480
catcgccacc atcgcttcac cggccacatg gagaaggaca tggcgtttgt gcctgccacc     540
gaggctgatc gcaaccagag gaagctggcc aacttgtaca tggacaagga gacggccgag     600
atgtttgagg atgtgcccat tgtccagctc gtcaagctca tcgcccacca gctgccggc      660 tggcagatgt acctcctctt caacgtctcc gccggtaagg gcagcaagca gtgggagact     720
ggcaagggcg gcatgggctg gttgagggtt agccactttg agccttcctc tgctgtgttc     780
cgcaactccg aggccatcta cattgccctg tccgatcttg gtctcatgat catgggctat     840
atcctctacc aggccgcgca ggttgttggc tggcagatgg taggtctgct gtacttccag     900
cagtacttct gggttcacca ttggttggtc gccatcactt acctccacca cacccacgag     960
gaagtccacc actttgacgc cgactcgtgg accttcgtca agggcgctct cgccaccgtc    1020
gaccgcgatt ttggcttcat tggcaagcac ctcttccaca acattatcga ccaccacgtc    1080
gtccaccact tgttccctcg catccccttc tactacgccg aagaagccac caactcgatc    1140
cgccccatgc tcgcccccct ctaccaccgc gacgaccgct ccttcatggg ccagctgtgg    1200
tacaacttca cccactgcaa gtgggtcgtt ccggacccc aggtccccgg cgcgcttatt    1260
tgggcgcaca ccgttcagag cacccagtaa                                      1290

<210> SEQ ID NO 20
<211> LENGTH: 1290
<212> TYPE: DNA
<213> ORGANISM: Neurospora crassa

<400> SEQUENCE: 20
atggcggtca ccacccgcag ccacaaggcc gcggccgcca ccgagcccga ggttgtcagc      60
accggcgttg acgccgtctc tgctgctgct ccctcctcct cctcctcctc ttccagccaa     120
aagtcggccg agcccatcga ataccccgac atcaagacca tccgcgacgc catccccgac     180
cactgcttcc gcccgcgcgt ctggatctcc atggcctact tcatccgcga cttcgccatg     240
gcctttggcc tcggctacct cgcctggcag tacatccccc tgatcgcctc caccccgctc     300
cgctacggcg cctgggctct gtacggctac ctccagggtc tcgtctgcac gggcatctgg     360
attctggcgc acgagtgcgg ccacggcgcc ttctcgaggc acacgtggtt caacaacgtc     420
atggggtgga ttggccactc cttcctcttg gtcccttact tcagctggaa gttcagccac     480
catcgccacc atcgcttcac cggccacatg gagaaggaca tggcgtttgt gcctgccacc     540

-continued

```
gaggctgatc gcaaccagag gaagctggcc aacttgtaca tggacaagga gacggccgag      600
atgtttgagg atgtgcccat tgtccagctc gtcaagctca tcgcccacca gctggccggc      660
tggcagatgt acctcctctt caacgtctcc gccggtaagg gcagcaagca gtgggagact      720
ggcaagggcg gcatgggctg gttgagggtt agccactttg agccttcctc tgctgtgttc      780
cgcaactccg aggccatcta cattgccctg tccgatcttg gtctcatgat catgggctac      840
atcctctacc aggccgcgca ggttgttggc tggcagatgg tgggtctgct gtacttccag      900
cagtacttct gggttcacca ttggttggtc gccatcactt acctccacca cacccacgag      960
gaagtccacc actttgacgc cgactcgtgg accttcgtca agggcgctct cgccaccgtc     1020
gaccgcgatt ttggcttcat tggcaagcac ctcttccaca acattatcga ccaccacgtc     1080
gtccaccact tgttccctcg catcccctc tactacgccg aagaagccac caactcgatc      1140
cgccccatgc tcggccccct ctaccaccgc gacgaccgct ccttcatggg ccagctgtgg     1200
tacaacttca cccactgcaa gtgggtcgtt ccggaccccc aggtcccccgg cgcgcttatt     1260 tgggcgcaca ccgttcagag cacccagtaa                                     1290
```

```
<210> SEQ ID NO 21
<211> LENGTH: 2391
<212> TYPE: DNA
<213> ORGANISM: Mortierella alpina

<400> SEQUENCE: 21
```

```
caggatcggc ggcagcggtg gcaggagcca aggagcaggc tccagacgct gcttaggaac       60
cggggacccg ggagtgcccg caccctgagc tctcagctcc ggaggcgtca tggcagagta      120
cggaactctc cttcaggacc tgaccaacaa catcaccctt gaagatctgg aacagctcaa      180
gtcagcctgc aaggaggaca tccccagtga gaagagtgag gagatcacca caggcagcgc      240
ctggtttagc ttcctggaga gccacaacaa gctggacaaa gacaacctct cctacataga      300
gcacatcttt gagatatctc gccgtcctga cctcctcact atggtggttg actacagaac      360
ccgtgtgctg aagatctctg aggaggagga gctggacacc aagctaaccc gtattcccag      420
tgccaagaag tacaaagaca ttatccggca gccctctgaa gaagaaatca tcaaattggc      480 tccccccacca agaaggcct gaacaagggg gaggaagagg aggaaggttg atcttcatc      540 agaccactcc cttccccatc ctcaatggga ggggctaggg caaccccctg ctccgtaccc      600
atttactaac ttggtcctaa cccttactat gcgcgtgtgt gtcggtgtgc gcacgctctg      660
gctgtctgtc tgtctagctc atctagttcc tcctcctcat gagggggattg gaggcaaggg      720 aggggggagct taattccccc cactatagggg ggaggtggac gctttttcta tgtaaacaga      780
aattggcaca ttcctcctcc ttctccccctt tcctccactc tttccccaca tcttatgga      840 agcagaaagg acctgcatt tcctacactg aggagctatg gtgaagatga ggtatgggag       900
agatggttgt atctaaagaa aaccagtggg gaaggaaggt aaagaggcca ctcaacctcc      960
acctggtaag ggacaaagaa aagccaggac tcagtgtttg tatctctatg ctggactggt     1020
tagaagccag cttcccgctg ttcccttagg ctgaggtcct gagtgccaat gggccctcct     1080
tatgcccttg ttatgggcct gggatgcgga tgagccagaa atcttaatga aagaccact      1140 cgatcctttc ctggtcccaa agatcaaacc ccaatggaga agccagcatt tactgtcccc     1200
caaccttctg ctctggagag acgatgccgg gaccatgcac tactgagcct gagctaggga     1260
cgcaggcaga gacaggccca cttcctgctc tcagtttct aaatacagac tgttggataa      1320
actgacctgg agcctaggga gattggggga tgagatcctt aggttttaac cccaacctgc     1380
```

```
ccacaaccta cagagtattg taggcaacct ttccactctc cagtttagaa ttctccaagc    1440
aagtagttaa ttacagtgtt tcctttgcac tgaccaccac cctgattcaa tccaggaagg    1500
gactggtaac ctttctcatt tgggtttgtg gatgccacac agccaagtca ctagagtgca    1560
gtgagtgaac ccagcctcct ccctgtccca agatgcccct tcccatcttg accgtgctaa    1620
ctgtgtgtac atatatattc tacatatatg tatattaaac ccgcactgcc atgtctgccc    1680
ttttttgtgg tttttagcat taacttattg tctaggccag agcgggagtg ggaggggatg    1740
ccacagaaag gaagtggcag agccaaattg ttacagagtc caaacagaaa acacatttca    1800
actaaccaca acaaatgtta catttacatg tgagctaaga gacaatttag agaaagatga    1860
aggtaggtgc ttttaggatg tgggagcaaa acttcacagg gaggggagga atggctgtca    1920
gaagagggtt cttgaagcca gactgactag agcaccctca gttcctagct gagcccagat    1980
tgcccatctc ctctggccac tgctgcagac acctgcctta actctcacac ctcgaagact    2040
ccagttttgc cttaaaggtc cttcctaaat ctccctagtc ttgcctggca tctcctttaa    2100
gacaagaaat ccttgtacaa ctgggtggga gaaaggaact ctgggtaaca tccttccttc    2160
tggggtgttc catgggagca ggagtgagac ggcgcttccc ttatggaaga gggaggagac    2220
agggtgcttc tcagaagctt ctctgtaagg caaaaaccaa actttaaaca gactaacctg    2280
ccctaatata ctcaccccct cgtgctgctg tgaggttgct cctagcctgt gctcctctgt    2340
ctgcagcgtg cacagccttg ttctaaccct ggaataaagg tgactgactc t             2391

<210> SEQ ID NO 22
<211> LENGTH: 522
<212> TYPE: DNA
<213> ORGANISM: Artificial Sequence
<220> FEATURE:
<221> NAME/KEY: modified_base
<222> LOCATION: (200)...(511)
<223> OTHER INFORMATION: N = A, C, G, or T
<220> FEATURE:
<223> OTHER INFORMATION: Description of Artificial Sequence:  Synthetic
      Primer

<400> SEQUENCE: 22
ttacagtaca gtcaatcacc tttattccag ggttagaaca aggccgtgca cactgcagac      60
aggagcacag gatggggaca atctcacagc cgtacagggt gggagggcag gttagtcttt     120
ttaggttatt tttgccttac agagagattt ctagactctg ctggaaatga ccctgtctcc     180
cttctcccat ctccccctc ctctcctcan agaaggctcc tattccttcc tcctcttccc     240
cctctcgctc tcgctcgctc tcacgcacat tctcacatca cgtaatcctg accggaagga     300
cagtcgtgct cagctccccc ctcccaattc tacaagtgcc tctcggtcct ggagggagaa     360
gcagacaggg ctggggcatc tcggggaggt cctttaaggc aaaactgngg agtactccag     420
gtgtccgtgt taaggcaggt gtccccanca ntggccaaaa gggacggctg ggctgggctg     480
gctgggcgtg caaggttgtt ccnggcccgn nggtttcttc tt                        522
```